United States Patent [19]

Beck

[11] Patent Number: 5,814,453
[45] Date of Patent: Sep. 29, 1998

[54] DETECTION OF FUNGAL PATHOGENS USING THE POLYMERASE CHAIN REACTION

[75] Inventor: James Joseph Beck, Cary, N.C.

[73] Assignee: Novartis Finance Corporation, New York, N.Y.

[21] Appl. No.: 887,480

[22] Filed: Jul. 2, 1997

Related U.S. Application Data

[63] Continuation-in-part of Ser. No. 722,187, filed as PCT/US95/04712, Apr. 19, 1995 published as WO95/29260.

[51] Int. Cl.$^6$ ............................. C12Q 1/68; C12P 19/34; C07H 21/04
[52] U.S. Cl. ..................... 435/6; 435/91.2; 536/23.1; 536/24.3; 536/24.32; 536/24.33
[58] Field of Search ........................ 435/6, 91.2, 810; 536/23.1, 24.3, 24.32, 24.33

[56] References Cited

U.S. PATENT DOCUMENTS

| | | | |
|---|---|---|---|
| 4,683,195 | 7/1987 | Mullis et al. | 435/91.2 |
| 4,683,202 | 7/1987 | Mullis | 435/91.2 |
| 5,585,238 | 12/1996 | Ligon et al. | 435/6 |
| 5,707,802 | 1/1998 | Sandhu et al. | 435/6 |

FOREIGN PATENT DOCUMENTS

WO 91/14001  9/1991  WIPO .

OTHER PUBLICATIONS

Bateman et al., "Relationships Among Fusarium SPP. Estimated by Comparing Restriction Fragment Length Polymorphisms in Poly Merase Chain Reaction–Amplified Ribosomal DNA". *Cereal Research Communications*, 25(3/2): 577–578 (1997).

Nicholson et al., "Detection and Qualification of Individual Fungal Species in Fusarium Disease Complexes of Cereals by Polymerase Chain Reaction (PCR)", *Cereal Research Communications*, 25(3/1): 477–482 (1997).

Nicholas et al., "Restriction fragment length polymorphism analysis of variation in Fusarium species causing ear blight of cereals", *Plant Pathology* 42: 905–914 (1993).

Schesser et al., "Use of Polymerase Chain Reaction To Detect the Take–All Fungus, *Gaeumannomyces graminis*, in Infected Wheat Plants", *Applied and Environ. Microbiol.*, 57(2): 553–556 (1991).

Schilling et al., "Polymerase Chain Reaction–Based Assays for Species–Specific Detection of *Fusarium Culmorum*, *F. graminearum*, and *F. avenaceum*", *Phytopathology*, 86(5): 515–527 (1996).

Stratagene Catalog, 1988, p. 39.

Tisserat et al., "Selective Amplification of rDNA Internal Transcribed Spacer Regions to Detect *Ophiosphaerella korrae* and *O. herpotricha*", *Phytopathology*, 84(5): 478–482 (1994).

White, T.J., et al., "Amplification and Direct Sequencing of Fungal Ribosomal RNA Genes for Phylogenetics", In: *PCR Protocols*; Academic Press Inc., pp. 315–322 (1990).

Xue et al., "Pathotype Identification of *Leptosphaeria maculans* with PCR and oligonucleotide primrers from ribosomal internal transribed spacer sequences", *Physiological and Molecular Plant Pathology*, 41: 179–188 (1992).

GenBank Accession No. U04237, computer printout, Jan. 3, 1994.

O'Donnell, Curr. Genetics 22, 213–220 (1992).

Zuechtungsforschung 1(2), 328–331 (1995).

*Primary Examiner*—Kenneth R. Horlick
*Attorney, Agent, or Firm*—J. Timothy Meigs

[57] ABSTRACT

Internal Transcribed Spacer (ITS) DNA sequences from the ribosomal RNA gene region are described for different species and strains of cereal fungal pathogens, including Septoria, Pseudocercosporella, Fusarium, Microdochium, and Mycosphaerella. Specific primers from within these sequences are identified as being useful for the identification of the fungal isolates using PCR-based techniques.

21 Claims, 9 Drawing Sheets

```
              10        20        30        40        50        60
               -         -         -         -         -         -
pCRSTRIT1.con  TCCGTAGGTGAACCTGCGGAAGGAGGATCATTA---------------------------
pCRSNOD31.con  TCCGTAGGTGAACCTGCGGAAGGAGGATCATTA---------------------------
pCRW2-1.con    TCCGTAGGTGAACCTGCGGAAGGATCATTAATAGAGCAATGAACAGACAGCCCCCGGGA
pCRW5-1.con    TCCGTAGGTGAACCTGCGGAAGGATCATTAATAGAGCAATGAACAGACAGCGCCCTGGGA
pCRR1-21.con   TCCGTAGGTGAACCTGCGGAAGGATCATTAATAGAGCAATGAACAGACAGCGCCCTGGGA
Mfij.con       TCCGTAGGTGAACCTGCGGAAGGATCATTAATAGAGCAATGAATGATAGACAGGCCCGGGA
Mmus.con       TCCGTAGGTGAACCTGCGGGGGGATCATTA---------------------------

70        80        90       100       110       120
               -         -         -         -         -         -
pCRSTRIT1.con  ----C-----------------CG-AGCGAGG------GCCTCCGGGTCCG---------
pCRSNOD31.con  ----CACTCAGTAGTTTACTACTG-TAAAAGG------GGCTGTGTTAGTCTGTATAGCGAA
pCRW2-1.con    GAAATCCTGGGGGCTACCCTACTT-GGTAGGGTTTAGAGTCGTCAGGCCGCTCGGAGAAG
pCRW5-1.con    GAAATCCTGGGGGCTACCCTACTTCGGTAGGGTTTAGAGTCGTCAGGCCTCTCGGAGAAG
pCRR1-21.con   GAAATCCTGGGGGCCACCCTACTTCGGTAAGGTTTAGAGTCGTCGGGCCTCTCGGAGAAG
Mfij.con       ----C-----------------CG-AGTGAGG------GCTCACG---CCCG--------
Mmus.con       ----C-----------------CG-AGTGAGG------GCTCACC---CCCG--------

130       140       150       160       170       180
               -         -         -         -         -         -
pCRSTRIT1.con  ----------ACCTCCAACCCTTTGTGAACACAT-CCCGTTGCTTCGG-GGGCGACCCTG
pCRSNOD31.con  GCTGAT---GAGCAGCTGCCTCCACCCTTTATCCAC--CTTGTCTTTTGCG-TACCCACGTTT
pCRW2-1.con    CCTGGTTCAGACCTTCCACCCTTCCACCCTTGAATAAATTACC--TTTGTTGCTTTGGCAGGGCGCCTCG
pCRW5-1.con    CCTGGTTCAGACCTTCCACCCTTCCACCCTTGAATAAATTACC--TTTGTTGCTTTGGCAGGGCGCCTCG
pCRR1-21.con   CCTGGTCCAGACCTTCCACCCTTCCACCCTTGAATAATTACC--TTTGTTGCTTTGGCAGGGCGCCTCG
Mfij.con       ----------ACCTCCAACCCTTTGTGAACCACACTTGTGAACCAACTTGTTGCTTCGG-GGGCGACCTGC
Mmus.con       ----------ACCTCCAACCCTTTGTGAACCACA-CCTGTTGCTTCGG-GGGCGACCCTG
```

FIGURE 1A

```
                190       200       210       220       230       240
                 |         |         |         |         |         |
pCRSTRIT1.con   C------------------CGGGCGCCCCCGGAG----GACCACCAAA----AAAC---ACTG
pCRSNOD31.con   C------------CTCGGCAGGCTTGCCTGCCG----GTTGGACAAATTTATAACC---TTTT
pCRW2-1.con     C------------GCCAGCGGCTTCGGCTGTTGAGCTGCCAGA----GGACCACAACT
pCRW5-1.con     C------------GCCAGCGGCTTCGGCTGTTGAGCTGCCAGA----GGACCACAACT
pCRR1-21.con    C------------GCCAGCGGCTTCGGCTGTTGAGCTGCCAGA----GGACCACAACT
Mfij.con        C------------GTCGGCGGGCGCCCCCGGAG----GCCGTCT----AAAC---ACTG
Mmus.con        CCGGCGAACTTGTCGCCGGGCGCCCCGGGGCCCCCGGAG----GTCTCCT-------TAAC---ACTG 250       260       270       280       290       300
                 |         |         |         |         |         |
pCRSTRIT1.con   CATCTCTGCGTCGGAGTTT---ACGA---GTAAATCGAAACAAAACTTTCAACAACGGATCT
pCRSNOD31.con   TAATTTCAATCAGGTCGTCTGAA--AA---ACTTAATATAATAGT-TAAAACTTTCAACAACGGATCT
pCRW2-1.con     CTTGTTTTTAGTGATGTCTGAG--TACTATATATAATAGT-TAAAACTTTCAACAACGGATCT
pCRW5-1.con     CTTGTTTTTAGTGATGTCTGAG--TACTATATATAATAGT-TAAAACTTTCAACAACGGATCT
pCRR1-21.con    CTTGTTTTTAGTGATGTCTGAG--TACTATATATAATAGT-TAAAACTTTCAACAACGGATCT
Mfij.con        CATCTTTGCGTCGGAGTTT---A-AA--ACAAATCGAA--CAAAACTTTCAACAACGGATCT
Mmus.con        CATCTCTGCGTCGGAGTTC---C--AA--ACAAATCGGA-CAAAACTTTCAACAACGGATCT 310       320       330       340       350       360
                 |         |         |         |         |         |
pCRSTRIT1.con   CTTGGTTCTCTGGCATCGATGAAGAACGCAGCGAAATGCGATAAGTAATGTGAATTGCAGAA
pCRSNOD31.con   CTTGGTTCTCTGGCATCGATGATGAAGAACGCAGCGAAATGCGATAAGTAGTGTGAATTGCAGAA
pCRW2-1.con     CTTGGTTCTCTGGCATCGATGAAGAACGCAGCGAAATGCGATAAGTAGTGTGAATTGCAGAA
pCRW5-1.con     CTTGGTTCTCTGGCATCGATGAAGAACGCAGCGAAATGCGATAAGTAATGTGAATTGCAGAA
pCRR1-21.con    CTTGGTTCTCTGGCATCGATGATGAAGAACGCAGCGAAATGCGATAAGTAATGTGAATTGCAGAA
Mfij.con        CTTGGTTCTCTGGCATCGATGAAGAACGCAGCGAAATGCGATAAGTAATGTGAATTGCAGAA
Mmus.con        CTTGGTTCTCTGGCATCGATGAAGAACGCAGCGAAATGCGATAAGTAATGTGAATTGCAGAA
```

FIGURE 1B

```
                     370       380       390       400       410       420
                       |         |         |         |         |         |
pCRSTRIT1.con  TTCAGTGAATCATCGAATCTTTGAACGCACATTGCGCCCCTGTATTCCGGGGGCATG
pCRSNOD31.con  TTCAGTGAATCATCGAATCTTTGAACGCACATTGCGCCCCTTGTATTCCATGGGCATG
pCRW2-1.con    TTCAGTGAATCATCGAATCTTTGAACGCACATTGCGCCTCTGTATTCCGGGGGCATG
pCRW5-1.con    TTCAGTGAATCATCGAATCTTTGAACGCACATTGCGCCCTCTGTATTCCGGGGGCATG
pCRR1-21.con   TTCAGTGAATCATCGAATCTTTGAACGCACATTGCGCCCTCTGTATTCCGGGGGCATG
Mfij.con       TTCAGTGAATCATCGAATCTTTGAACGCACATTGCGCCCTTGGTATTCCGAAGGGCATG
Mmus.con       TTCAGTGAATCATCGAATCTTTGAACGCACATTGCGCATTTGGCATTCCGAAGGGCATG 430       440       450       460       470       480
                       |         |         |         |         |         |
pCRSTRIT1.con  CCCGTTCGAGCGTCATT-ACACCACTCCAGCCTC-GCTGGGTATTGGGCGTCTTTTCGCG
pCRSNOD31.con  CCTGTTCGAGCGTCATT--TGTACCCTCAAGCTCT-GCTTGGTGTTGGTGTGTT------
pCRW2-1.con    CCTGTTCGAGCGTCATTCATTATAACCACTCAAGCTCT-GCTTGGTCTTGGTATTGG--GT-----
pCRW5-1.con    CCTGTTCGAGCGTCATTCATTATAACCACTCAAGCTCT-GCTTGGTCTTGGTATTGG--GT-----
pCRR1-21.con   CCTGTTCGAGCGTCATTCATTATAACCACTCAAGCTCT-GCTTGGTCTTGGTATTGG--GT-----
Mfij.con       CCTGTTCGAGCGTCATT--TCACCACTCAAGCCTG-GCTTGGTATTGGGCGTC---------
Mmus.con       CCTGTTCGAGCGTCATT--TCACCACTCAAGCCTA-GCTTGGTATTGGGCGCC---------

490       500       510       520       530       540
                       |         |         |         |         |         |
pCRSTRIT1.con  GGGGATCACTCCCCCGCGCCTCAAAGTCTCC------GGCTGAGCGGTCTCGTCTCC
pCRSNOD31.con  ----TGTCCTCCTCCCGCGCCTCCAGTGTTTGGACTCGCCCTTAAAA-TAATTGGCAGCC--AGTGTTT
pCRW2-1.con    ----TCGCGTCCTCGCGGCCTCTAAATCAGT---------GGCGGTGCCTGT-CGGCTCT
pCRW5-1.con    ----TCGCGTCCTCGCGGCCTCTAAATCAGT---------GGCGGTGCCTCT-CGGCTCT
pCRR1-21.con   ----TCGCGTCTTCGCGGCCTCTAAATCAGT---------GGCGGTGCCTCT-CGGCTCT
Mfij.con       ----GCGGTTCTTCGCGGCCTCGCGCCTTAAAGTCTCC------GGCTGAGCTGTC-CGTTCT
Mmus.con       ----GCGGTGCCGGCGCGCCCCCAAAGTCTCC------CGGCTAAGCCGTC-CGTCTCT
```

FIGURE 1C

```
                    550       560       570       580       590       600
                    |         |         |         |         |         |
pCRSRTRIT1.con      CAGCGTTGTGTGG--CATCACGTCTCGCCGCGGAGTTCACGAGCCCTCAC----GGCCGTTA
pCRSNOD31.con       TGGTATTGAAGCGCAGCACAAGTCGCGATTCGTA--ACAAACACTTGC----GTCCACAA
pCRW2-1.con         ACGCGTAGTAATACTCCTCGGCGATTGAGTCCGGT--AGTTTACTTGCCAGTAACCCCCA
pCRW5-1.con         ACGCGTAGTAATACTCCTCGGCGATTGAGTCCGGT--AGTTTACTTGCCAGTAACCCCCA
pCRR1-21.con        ACGCGTAGTAATACTCCTCGGCGATTGAGTCCGGT--AGTTTACTTGCCAGCAACCCCCA
Mfij.con            AAGCGTTGTGG-ATCTTTCAATTCGCTTCGGAGT---GCGGGTGGCCGC----GGCCGTTA
Mmus.con            AAGCGTTGTGG-ATTTTTCAGTTCGCTTCCGGAGC----GCGGGTGGCCGC----GGCCGTTA 610       620       630       640       650       660
                    |         |         |         |         |         |
pCRSRTRIT1.con      AATCACA------CCTCAGGTTGACCTTCGGATCGGTAGGATACCCGCTGAACTTAAGCAT
pCRSNOD31.con       GCCT--T-----TTTAACTTTTGACCTTCGGATCAGTCAGGATACCCGCTGAACTTAAGCAT
pCRW2-1.con         ATTT--T-----TTACAGGTTGACCTTCGGATCAGTCAGGATACCCGCTGAACTTAAGCAT
pCRW5-1.con         ATTT--T-----TTACAGGTTGACCTTCGGATCAGTCAGGATACCCGCTGAACTTAAGCAT
pCRR1-21.con        ATTT--T-----TTACAGGTTGACCTTCGGATCAGTCAGGATACCCGCTGAACTTAAGCAT
Mfij.con            AATC--T-----TTTATTCAAAGGTTGACCTTCGGATCAGTCAGGATACCCGCTGAACTTAAGCAT
Mmus.con            AATC--T-----TCAAAGGTTGACCTTCGGATCAGTCAGGATACCCGCTGAACTTAAGCAT 670
                    |
pCRSRTRIT1.con      ATCAATAAGCGGAGGA
pCRSNOD31.con       ATCAATAAGCGGAGGA
pCRW2-1.con         ATCAATAAGCGGAGGA
pCRW5-1.con         ATCAATAAGCGGAGGA
pCRR1-21.con        ATCAATAAGCGGAGGA
Mfij.con            ATCAATAAGCGGAGGA
Mmus.con            ATCAATAAGCGGAGGA
```

FIGURE 1D

```
                           10              20              30              40              50              60
                           |               |               |               |               |               |
pCRSNOD31.con    TCC-GTAGGTGAACCTGCGGAAGGATCATTACACTCAGTAGTTTACTACTGTAAAAGGGG
SATITS.CON       TCCCGTAGGTGAACCTGCGGAAGGATCATTACACTCAGTAGTTTACTACTGTAAAGGAGG 70              80              90             100             110             120
                           |               |               |               |               |               |
pCRSNOD31.con    CTGTTAGTCTGTATAGCGCAAGCTGATGAGCAGCTGGCCTCTCTTTATCCACCCTGTCTT
SATITS.CON       CTGTTAGTCTGTATAGCGCAAGCTGATGAGCAGCTAGCCCTCTCTTTTATCCACCCTGTCTT 130             140             150             160             170             180
                           |               |               |               |               |               |
pCRSNOD31.con    TTGCGTACCCACGTTTCCTCGGCAGGCTTGCCTGCCGGTTGGACAAATTTATAACCTTTT
SATITS.CON       TTGCGTACCCACGTTTCCTCGGCAGGCTTGCCTGCCGATTGGACAAACCTATAACCTTTT 190             200             210             220             230             240
                           |               |               |               |               |               |
pCRSNOD31.con    TAATTTTCAATCAGCGTCTGAAAAACTTAATAATTACAACTTTCAACAACGGATCTCTTG
SATITS.CON       TAATTTTCAATCAGCGTCTGAAAAACTTAATAATTACAACTTTCAACAACGGATCTCTTG 250             260             270             280             290             300
                           |               |               |               |               |               |
pCRSNOD31.con    GTTCTGGCATCGATGAAGAACGCAGCGA-AATGCGATAAGTAGTGTGAATTGCAGAATTC
SATITS.CON       GTTCTGGCATCGATGAAGAACGCAGCGACAATGCGACAATGCGATAAGTAGTGTGAATTGCAGAATTC
```

FIGURE 2A

```
                          310        320        330        340        350        360
                           |          |          |          |          |          |
pCRSNOD31.con   AGTGAATCATCGAATCTTTGAACGCACATTGCGCCCCCTTGGTATTCCATGGGCATGCCT
SATITS.CON      AGTGAATCATCGAATCTTTGAACGCACATTGCGCCCCCTTGGTATTCCATGGGCATGCCT 370        380        390        400        410        420
                           |          |          |          |          |          |
pCRSNOD31.con   GTTCGAGCGTCATTTGTACCCTCAAGCTCTGCTTGGTGTGTTGTCCTCTCCCTA
SATITS.CON      GTTCGAGCGTCATTTGTACCCTCAAGCTCTGCTTGGTGTGTTGTCCTCTCCCTA 430        440        450        460        470        480
                           |          |          |          |          |          |
pCRSNOD31.con   GTGTTTGGACTCGCCCTTAAAATAATTGGCAGCCAGTGTTTTGGTATTGAAGGCGCAGCACA
SATITS.CON      GTGTTTGGACTCGCCCTTAAAATAATTGGCAGCCAGTGTTTTGGTAYTGAAGGCGCAGCACA 490        500        510        520        530        540
                           |          |          |          |          |          |
pCRSNOD31.con   AGTCGCGATTCGTAACAAACACTTGCGTCCACAAGCC~~TTTTAACTTTTGACCTCGGA
SATITS.CON      AGTCGCGATTCTTATCAAATACTTGCGTCCACAAGCCCTTTTTTTAACTTTTGACCTCGGA 550        560        570        580
                           |          |          |          |
pCRSNOD31.con   TCAGGTAGGATACCCGCTGAACTTAAGCATATCAATAAGCGGAGGA
SATITS.CON      TCAGGTAGGAG~ACC~GCTGA~CTTAA
```

FIGURE 2B

```
                       10         20         30         40         50         60
                       |          |          |          |          |          |
Fculm.con    ~~~~~~~~~~~~~~~~~~~~GAGGGATCATTACCGAGTTTACTRACTCCCAAACCCCTGTGA
Fgram.con    ~~~~~~~~~~~~~~~~~~~~~GATCATTACCGAGTTTACWSACTCCCAAACCCCTGTGA
Fpoae.con    ~~~~~~~~~~~~~~~~~~~~~GATCATTACCGAGTTTACWSACTCCCAAACCCCTGTGA
Mniv.con     ~~~~~~~~~~~~~~~~~~~~~GATCATTACCGAGTTTAC~AACTCCCAAACCCCTGTGA
PCRFmon1.con ~~~~~~~~~~~~~~~~~~~~~GATCATTACCGAGTTTAC~AACTCCCAAACCCCTGTGA 70         80         90        100        110        120
                       |          |          |          |          |          |
Fculm.con    TCCGTAGGTGAACCTGCGGAGGGATCAGCCCGCCCCGCCGCCCCGTAAAAAGGACGGCCCGCC
Fgram.con    TCCGTAGGTGAACCTGCGGAGGGATCAGCCCGCCCCGCCCCG~~~AAAGGACGGCCCGCC
Fpoae.con    TCCGTAGGTGAACCTGCGGAGGGATCAGCCCGCCCCGCKCCYYGTAAAACGGACGGCCCGCC
Mniv.con     ACTTACCAC~~TGTTGCCTCGGTGGAT~GGTGC~TGTCTCTCGGACGGTRCCACC~GCC
PCRFmon1.con ACATACCTT~ATGTTGCCTCGGCGGGATCAGCCCGCGCCCGCCTAAAAAGGACGGCCCGCC 130        140        150        160        170        180
                       |          |          |          |          |          |
Fculm.con    GCAGGAA~CCCTAAACTCTG~~~~~TTTTTAGTGGAACTTCTGAGTATAAAAACAATAA
Fgram.con    GCAGGAA~CCCTAAACTCTG~~~~TTTTTAGTGGAACTTCTGAGTATAAAAACAATAA
Fpoae.con    GCAGGAAACCCTAAACTCTG~~~~~TTTTTAGTGGAACTTCTGAGTATAAAAACAATAA
Mniv.con     GGTGGACTACCTAAACTCTGTTAATTTTTGYCAA~~~~TCTGAATCAAACTAAGAAATAA
PCRFmon1.con GCAGGAA~CCCTAAACTCTG~~~~~TTTTTAGTGGAACTTCTGAGTATAAAAACAATAA 190        200        210        220        230        240
                       |          |          |          |          |          |
Fculm.con    ATCAAAACTTTCAACAACGGATCTCTTGGTTCTGGCATCGATGAAGAACGCAGCAAAATG
Fgram.con    ATCAAAACTTTCAACAACGGATCTCTTGGTTCTGGCATCGATGAAGAACGCAGCAAAATG
Fpoae.con    ATCAAAACTTTCAACAACGGATCTCTTGGTTCTGGKCTCGGCATCGATGAAGAACGCAGCAAAATG
Mniv.con     GTTAAAACTTTCAACAACGGATCTCTTGGTTCTGGCATCGATGAAGAACGCAGCGAAATG
PCRFmon1.con ATCAAAACTTTCAACAACGGATCTCTTGGTTCTGGCATCGATGAAGAACGCAGCAAAATG
```

FIGURE 3A

```
                 250       260       270       280       290       300
                   |         |         |         |         |         |
Fculm.con    CGATAAGTAATGTGAATTGCAGAATTCAGTGAATCATCGAATCTTTGAACGCACATTGCG
Fgram.con    CGATAAGTAATGTGWATTGCAGAATTCAGTGAATCAWCGAATCTTTGAACGCWSATTGCK
Fpoae.con    CGATAAGTAATGTGAATTGCAGAATTCAGTGAATCATCGAATCTTTGAACGCACATTGCG
Mniv.con     CGATAAGTAATGTGAATTGCAGAATTCAGTGAATCATCGAATCTTTGAACGCACATTGCG
PCRFmon1.con CGATAAGTAATGTGAATTGCAGAATTCAGTGAATCATCGAATCTTTGAACGCACATTGCG 310       320       330       340       350       360
                   |         |         |         |         |         |
Fculm.con    CCCGCCAGTATTCTGGCGGGCATGCCTGTTCGAGCGTCATTTCAACCCTCAAGCCC~~~A
Fgram.con    MCCRCCAGTATTCTGGCGGGCATGCCTGTTCGAGCGTCATTTCAACCCTCAAGCCC~~~A
Fpoae.con    CCCGCCAGTATTCTGGCGGGCATGCCTGTTCGAGCGTCATTTCAACCCTCAAGCCC~~~A
Mniv.con     CCCATTAGTATTCTAGTGGGCATGCCTGTTCGAGCGTCATTTCAACCCTTAAGCCT~~~A
PCRFmon1.con CCCGCCAGTATTCTGGCGGGCATGCCTGTTCGAGCGTCATTTCAACCCTCAAGCCC~~~A 370       380       390       400       410       420
                   |         |         |         |         |         |
Fculm.con    GCTTGGTGTTGGG~A~~~~~GC~~~~TGCAGTCCTGCTG~~~CACTCCCCAAATACATTG
Fgram.con    GVTTGGTGTKGGGGA~~~~~RY~~~~TGCAGKCCTRYTK~~~CACTCCCCAAATAARTTG
Fpoae.con    GCTTGGTGTTGGG~A~~~~~TC~~~~TTGYGTKMAWWCR~~~CAKTCCCCAAATTGATTG
Mniv.con     GCTTAGTGTTGGGAGACTGCCTAATACGCAGCTCCTCAAAACCAGTGGCGGAGTCGGTTC
PCRFmon1.con GCTTGGTGTTGGG~A~~~~~GC~~~~TGCAGTCCTGCTG~~~CACTCCCCAAATACATTG 430       440       450       460       470       480
                   |         |         |         |         |         |
Fculm.con    GCGGTCACGTCGRAGCT~TCCATAGCGTAGTAATTTACATATCGTTACTGGTAATCGTCG
Fgram.con    GCGGTCACGTCGAA~CT~TCCATAGCGTAGTAAGTTACACATCGTTACTGGTAATCGTCG
Fpoae.con    GCGGTCACGTCGA~GCT~TCCATAGCGTAGTAATTTACACATCGTTACTGGTAATCGTCG
Mniv.con     GTGCTCTGAGCGTAGTAATTTTTTATCTCGCT~TCTGCAAGYCG~GACTGGCAACAGCCA
PCRFmon1.con GCGGTCACGTCGA~GCT~TCCATAGCGTAGTAATTTACACATCGTTACTGGTAATCGTCG
```

FIGURE 3B

```
                 490       500       510       520       530       540
                   |         |         |         |         |         |
Fculm.con     CGG~CYACGCCGTTAAACCCCAACTTCTGAATGTTGACCTCGGATCAGGTAGGAATACCC
Fgram.con     CGG~CTACGCCGTTAAACCCCAACTTCTGAATGTTGACCTCGGATCAGGTAGGAATACCC
Fpoae.con     CGG~CCACGCCGTTAAACCCCAACTTCTGAATGTTGACCTCGGATCAGGTAGGAATACCC
Mniv.con      TAAACCGCACCCTTCGGGGGCACTTTTTAATGGTTGACCTCGGATCAGGTAGGAATACCC
PCRFmon1.con  CGG~CCACGCCGTTAAACCCCAACTTCTGAATGTTGACCTCGGATCAGGTAGGAATACCC 550       560       570
                   |         |         |
Fculm.con     GCTGAA
Fgram.con     GCTGAA~~~~GGTA~~~~~~~~~~~~~~~~A
Fpoae.con     GCTGAACTTAAGCATATCAATAAGCGGAGGA
Mniv.con      GCTGAACTTAAGCATATCAATAAGCGGAGGA
PCRFmon1.con  GCTGAACTTAAGCATATCAATAAGCGGAGGA
```

FIGURE 3C

DETECTION OF FUNGAL PATHOGENS USING THE POLYMERASE CHAIN REACTION

This is a continuation-in-part of U.S. application Ser. No. 08/722,187, filed 15 Oct. 1996, which is an application under 35 U.S.C. §371 of PCT/US95/04712, filed 19 Apr. 1995 (published as WO 95/29260).

FIELD OF THE INVENTION

The present invention relates to the use of species-specific primers in polymerase chain reaction assays for the detection of fungal pathogens. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; Seed Sci. & Technol. 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; Proc. 1981 Brit. Crop Prot. Conf.) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and Mycosphaerella fijiensis to triazoles to mention just a few (Jones and Clifford; Cereal Diseases, John Wiley, 1983).

Cereal species are grown world-wide and represent a major fraction of world food production. Although yield loss is caused by many pathogens, the necrotizing pathogens Septoria and Pseudocercosporella are particularly important in the major cereal growing areas of Europe and North America (Jones and Clifford; Cereal Diseases, John Wiley, 1983). In particular, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

Four Septoria species parasitize the small grain species. *Septoria tritici* is the causative agent of leaf blotch and is virulent on wheat but also parasitizes triticale and rye. It typically causes leaf necrosis. *Septoria nodorum* is the causative agent of glume blotch and is parasitic on wheat, triticale, rye and barley and although mainly restricted to glumes is also found on leaf blades and sheaths. *Septoria avenae* is parasitic on oats, wheat and triticale and *Septoria passerinii* is restricted to barley. Septoria diseases occur in all wheat growing areas at economically important levels. Different Septoria diseases frequently occur concurrently within fields and on individual plants, where the disease symptoms may be collectively referred to as the "Septoria complex". Typically, the most commonly found species are *S. tritici* and *S. nodorum*. According to Wiese (1977; Compendium of Wheat Diseases, Amer. Phytopath. Soc. pages 42–45), the Septoria complex presently destroys nearly 2% of the world's wheat annually, the yield loss being mainly the result of impaired grain filling. Fungicide treatments can save up to 20% in cases of severe Septoria infection, but it is often difficult to distinguish between the different Septoria species at the onset of infection and this makes the decision whether or not to invest in fungicide use difficult because different cultivars display differing degrees of resistance to the various Septoria species.

The eyespot disease of cereals is caused by the fungus *Pseudocercosporella herpotrichoides* and is restricted to the basal culm of the plant. Wheat, rye, oats and other grasses are susceptible to the eyespot disease which occurs in cool, moist climates and is prevalent in Europe, North and South America, Africa and Australia. Wheat is the most susceptible cereal species, but isolates have been identified which are also virulent on other cereals. The R-strain of the fungus, for example, has also been isolated from rye and grows more slowly on wheat than the W-strain which has been isolated from wheat. Although eyespot may kill tillers or plants outright, it more usually causes lodging and/or results in a reduction in kernel size and number. Yield losses associated with eyespot are of even greater magnitude than those associated with *Septoria tritici* and *Septoria nodorum*. Typical control measures for eyespot include treatment with growth regulators to strengthen internodes, and fungicide treatment. However, the differing susceptibility of cultivars to different strains of the fungus render the predictive efficacy of fungicide treatments difficult.

Sigatoka leaf spot of banana occurs in two forms each of which is caused by a different fungus. The economically important Black Sigatoka is caused by *Mycosphaerella fijiensis*, whereas the less economically significant Yellow Sigatoka is caused by *Mycosphaerella musicola* (Johanson and Jeger, 1993; Mycol. Res. 97: 670–674). Black Sigatoka is the major problem in banana causing severe losses of 30% and more. Due to occurrence of fungicide resistance in *Mycosphaerella fijiensis*, usage of fungicide should best be limited to prevent the further occurrence of resistance. Consequently, the availability of diagnostic tools will provide an important means of identifying the appropriate circumstances in which to utilize fungicides without unnecessarily risking the development of further resistance.

*Microdochium nivale* (syns. *Fusarium nivale* and *Gerlachia nivalis*) is an important seed-borne pathogen of wheat (Hewett, 1983; Transactions of the British Mycological Society. Vol. 80: 185–186). In a recent study in the UK, *M. nivale* was found in over 90% of the wheat seed samples tested (Reeves and Wray, 1984; British Crop Protection Council Monograph. Vol. 57: 37–46). *M. nivale* also causes pink snow mold in wheat in the US, Canada, central Europe, and Scandinavia (1977; Compendium of Wheat Diseases, Amer. Phytopath. Soc. page 32). *M. nivale* and Fusarium spp. cause head blight (scab) in wheat spikes (1977; Compendium of Wheat Diseases, Amer. Phytopath. Soc. page 16). Significant yield losses may result from poor seed filling and floret sterility. *M. nivale* is also the predominate cause of foot rot disease in wheat (Pettitt, Parry and Polley, 1993; Mycological Research. Vol.97: 1172–1174).

Previously, the different Septoria species have been identifiable by examination under the microscope, and the identification of the different Pseudocercosporella strains has been possible only by pathological tests. Similarly, the unambiguous identification of *Mycosphaerella musicola* and *Mycosphaerella fijiensis* has been difficult, and even the isolation of mature perithecia does not always allow accurate identification (Pons, 1990; In: Sigatoka Leaf Spot Diseases of Banana, Eds. RA Fullerton and RH Stover, International Network for the Improvement of Banana and Plantain, France). Currently immunodiagnostic kits utilizing ELISA technology are routinely used to identify *Septoria tritici*, *Septoria nodorum*, *Pseudocercosporella herpotrichoides* and other pathogen, but this technology lacks the accuracy, detection limit and ability to distinguish different isolates of the instant invention. In consequence, the development of a DNA test for the rapid identification of different strains of these fungi offers real advantages not only to fungal taxonomists, but also for disease management and selective fungicide use in the field.

In view of the above, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase such as those caused by *Septoria nodorum* or *Septoria tritici* on wheat and *Mycosphaerella fijiensis* on banana.

In a preferred embodiment, the invention provides ITS 1 and ITS2 DNA sequences for the pathogens *Septoria tritici*, *Septoria nodorum*, *Pseudocercosporella herpotrichoides* strain W (two variants), *Pseudocercosporella herpotrichoides* strain R, *Mycosphaerella fijiensis*, *Mycosphaerella musicola*, *Septoria avenae* f.sp. triticea, *Fusarium graminearum, Fusarium culmorum, Fusarium moniliforme* and *Microdochium nivale*. In another preferred embodiment, the invention provides ITS-derived diagnostic primers for the detection of these fungal pathogens.

Kits useful in the practice of the invention are also provided. The kits find particular use in the identification of Septoria, Pseudocercosporella, Fusarium, Microdochium and Mycosphaerella pathogens.

DESCRIPTION OF THE FIGURES

FIG. 1 Sequence alignment of the ITS regions from *Septoria tritici* (SEQ ID NO:1), *Septoria nodorum* (SEQ ID NO:2), *Pseudocercosporella herpotrichoides* strain W (variant W2- 1) (SEQ ID NO:3), *Pseudocercosporella herpotrichoides* strain W (variant W5-1) (SEQ ID NO:47), *Pseudocercosporella herpotrichoides* strain R (SEQ ID NO:4), *Mycosphaerella fijiensis* (SEQ ID NO:5), and *Mycosphaerella musicola* (SEQ ID NO:6).

FIG. 2 Sequence alignment of the ITS regions from *Septoria nodorum* (SEQ ID NO:2) and *Septoria avenae* f.sp. *triticea* (SEQ ID NO:86).

FIG. 3 Sequence alignment of the ITS regions from *Fusarium culmorum* (SEQ ID NO:82), *Fusarium graminearum* (SEQ ID NO:83), *Fusarium poae* (SEQ ID NO:96), *Microdochium nivale* (SEQ ID NO:85), and *Fusarium moniliforme* (SEQ ID NO:84).

BRIEF DESCRIPTION OF THE SEQUENCES IN THE SEQUENCE LISTING

SEQ ID NO:1 DNA sequence of the ITS region PCR-amplified from *Septoria tritici*, comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:2 DNA sequence of the ITS region PCR-amplified from *Septoria nodorum*, comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:3 DNA sequence of the ITS region PCR-amplified from *Pseudocercosporella herpotrichoides* strain W (variant W2- 1), comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:4 DNA sequence of the ITS region PCR-amplified from *Pseudocercosporella herpotrichoides* strain R, comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:5 DNA sequence of the ITS region PCR-amplified from *Mycosphaerella fijiensis*, comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:6 DNA sequence of the ITS region PCR-amplified from *Mycosphaerella musicola*, comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:7 Oligonucleotide Primer JB433.
SEQ ID NO:8 Oligonucleotide Primer JB434.
SEQ ID NO:9 Oligonucleotide Primer JB525.
SEQ ID NO:10 Oligonucleotide Primer JB527.
SEQ ID NO:11 Oligonucleotide Primer JB445.
SEQ ID NO:12 Oligonucleotide Primer JB446.
SEQ ID NO:13 Oligonucleotide Primer JB526.
SEQ ID NO:14 Oligonucleotide Primer JB536.
SEQ ID NO:15 Oligonucleotide Primer JB537.
SEQ ID NO:16 Oligonucleotide Primer JB538.
SEQ ID NO:17 Oligonucleotide Primer JB539.
SEQ ID NO:18 Oligonucleotide Primer JB540.
SEQ ID NO:19 Oligonucleotide Primer JB541.
SEQ ID NO:20 Oligonucleotide Primer JB542.
SEQ ID NO:21 Oligonucleotide Primer JB543.
SEQ ID NO:22 Oligonucleotide Primer JB544.
SEQ ID NO:23 Oligonucleotide Primer JB547.
SEQ ID NO:24 Oligonucleotide Primer JB548.
SEQ ID NO:25 Oligonucleotide Primer JB442.
SEQ ID NO:26 Oligonucleotide Primer JB443.
SEQ ID NO:27 Oligonucleotide Primer JB545.
SEQ ID NO:28 Oligonucleotide Primer JB546.
SEQ ID NO:29 Oligonucleotide Primer JB549.
SEQ ID NO:30 Oligonucleotide Primer JB444.
SEQ ID NO:31 Oligonucleotide Primer JB451.
SEQ ID NO:32 Oligonucleotide Primer JB440.
SEQ ID NO:33 Oligonucleotide Primer JB449.
SEQ ID NO:34 Oligonucleotide Primer JB448.
SEQ ID NO:35 Oligonucleotide Primer JB441.
SEQ ID NO:36 Oligonucleotide Primer JB450.
SEQ ID NO:37 Oligonucleotide Primer JB452.
SEQ ID NO:38 Oligonucleotide Primer ITS1.
SEQ ID NO:39 Oligonucleotide Primer ITS52.
SEQ ID NO:40 Oligonucleotide Primer ITS3.
SEQ ID NO:41 Oligonucleotide Primer ITS4.
SEQ ID NO:42 Oligonucleotide Primer OPB-12.
SEQ ID NO:43 Oligonucleotide Primer OPE-6.
SEQ ID NO:44 Oligonucleotide Primer OPE-12.
SEQ ID NO:45 Oligonucleotide Primer OPE-19.
SEQ ID NO:46 Oligonucleotide Primer OPE-15.
SEQ ID NO:47 DNA sequence of the ITS region PCR-amplified from *Pseudocercosporella herpotrichoides* strain W (variant W5-1), comprising in the 5'-3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:48 M13 Universal-20 Primer.
SEQ ID NO:49 Reverse Primer used in Example 2.
SEQ ID NO:50 Oligonucleotide Primer JB563.
SEQ ID NO:51 Oligonucleotide Primer JB564.
SEQ ID NO:52 Oligonucleotide Primer JB565.
SEQ ID NO:53 Oligonucleotide Primer JB566.
SEQ ID NO:54 Oligonucleotide Primer JB567.
SEQ ID NO:55 Oligonucleotide Primer JB568.
SEQ ID NO:56 Oligonucleotide Primer JB569.
SEQ ID NO:57 Oligonucleotide Primer JB570.
SEQ ID NO:58 Oligonucleotide Primer JB571.
SEQ ID NO:59 Oligonucleotide Primer JB572.
SEQ ID NO:60 Oligonucleotide Primer JB573.
SEQ ID NO:61 Oligonucleotide Primer JB574.
SEQ ID NO:62 Oligonucleotide Primer JB575.
SEQ ID NO:63 Oligonucleotide Primer JB576.
SEQ ID NO:64 Oligonucleotide Primer JB577.
SEQ ID NO: 65 Oligonucleotide Primer JB578.
SEQ ID NO:66 Oligonucleotide Primer JB538'.
SEQ ID NO:67 Oligonucleotide Primer JB539'.
SEQ ID NO:68 Oligonucleotide Primer W130.
SEQ ID NO:69 Oligonucleotide Primer R130.
SEQ ID NO:70 Oligonucleotide Primer JB538'15.
SEQ ID NO:71 Oligonucleotide Primer JB539'15
SEQ ID NO:72 Oligonucleotide Primer JB553.
SEQ ID NO:73 Oligonucleotide Primer JB554.
SEQ ID NO:74 Oligonucleotide Primer JB555.
SEQ ID NO:75 Oligonucleotide Primer JB556.
SEQ ID NO:76 Oligonucleotide Primer JB 561.
SEQ ID NO:77 Oligonucleotide Primer JB562.
SEQ ID NO:78 Oligonucleotide Primer JB559.
SEQ ID NO:79 Oligonucleotide Primer JB560.
SEQ ID NO:80 Oligonucleotide Primer JB557.
SEQ ID NO:81 Oligonucleotide Primer JB558.
SEQ ID NO:82 Consensus DNA sequence of the ITS region PCR-amplified from *Fusarium culmorum* isolates R-5106, R-5126 and R-5146, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:83 Consensus DNA sequence of the ITS region PCR-amplified from *Fusarium graminearum* isolates R-8417, R-8422 and R-8546, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:84 DNA sequence of the ITS region PCR-amplified from *Fusarium moniliforme* isolate 4551, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:85 Consensus DNA sequence of the ITS region PCR-amplified from *Microdochium nivale* isolates 72, 520, and 18222, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:86 DNA sequence of the ITS region PCR-amplified from *Septoria avenae* f. sp. *triticea*, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:87 Oligonucleotide Primer JB605.
SEQ ID NO:88 Oligonucleotide Primer JB606.
SEQ ID NO:89 Oligonucleotide Primer JB607.
SEQ ID NO:90 Oligonucleotide Primer JB609.
SEQ ID NO:91 Oligonucleotide Primer JB610.
SEQ ID NO:92 Oligonucleotide Primer JB611.
SEQ ID NO:93 Oligonucleotide Primer JB612.
SEQ ID NO:94 Oligonucleotide Primer JB613.
SEQ ID NO:95 Oligonucleotide Primer JB614.
SEQ ID NO:96 Consensus DNA sequence of the ITS region PCR-amplified from *Fusarium poae* isolates T-427, T-534, and T-756, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA, gene regions of particular fungal pathogens as well as primers derived from these regions that are capable of identifying the particular pathogen. These ITS DNA sequences from different pathotypes within a pathogen species or genus, which vary between the different members of the species or genus can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers were able to distinguish numerous races of *Gremmeniella abietina*, the causal agent of scleroderris canker in conifers.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units each of which encodes three mature subunits of 18S (small subunit), 5.8S, and 28S (large subunit). These subunits are separated by two Internal Transcribed Spacers, ITS 1 and ITS2, of around 300 bp (White et al, 1990; In: PCR Protocols; Eds.: Innes et al; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Particular DNA sequences of interest include ITS DNA sequences from Septoria, particularly, *Septoria nodorum* and *Septoria tritici*; Mycosphaerella, particularly *Mycosphaerella fijiensis* and *Mycosphaerella musicola*; Pseudocercosporella, particularly *Pseudocercosporella herpotrichoides*, more particularly for the W-strain and the R-strain of *Pseudocercosporella herpotrichoides*, Fusarium, particularly *F. graminearum, F. culmorum, F. moniliforme, F. poae*, and *Microdochium nivale*. Such ITS DNA sequences as well as primers of interest are given in SEQ ID NO: 1–47 and SEQ ID NO.: 50–96. The sequences find use in the PCR-based identification of the pathotypes of interest.

Methods for the use of the primer sequences of the invention in PCR analysis are well known in the art. For example, see U.S. Pat. Nos. 4,683,195 and 4,683,202 as well as Schlesser et al. (1991) *Applied and Environ. Microbiol.* 57: 553–556. See also, Nazar et al. (1991; *Physiol. and Molec. Plant Pathol.* 39: 1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674) who used similar techniques to distinguish the banana pathogens *Mycosphaerella fijiensis* and *Mycospharella musicola.*

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2: 17–20; Lee et al. (1990) *Fungal Genetics Newsletter* 35: 23–24; and Lee and Taylor (1990) In: *PCR Protocols: A Guide to Methods and Applications*, Innes et al. (Eds.); pages 282–287.

Alternatively, the ITS sequences of interest can be determined by PCR amplification. In an exemplified embodiment, primers to amplify the entire ITS region were designed according to White et al. (1990; In: PCR Protocols; Eds.: Innes et al. pages 315–322), and the amplified ITS sequence was subcloned into the pCRII cloning vector. The subcloned sequence included the left hand ITS (ITS 1), the right hand ITS (ITS2) as well as the centrally located 5.8S rRNA gene. This was undertaken for *Septoria nodorum* and *Septoria tritici*, numerous Pseudocercosporella isolates and *Mycosphaerella fijiensis, Mycosphaerella musicola, Septoria avenae triticea, F. graminearum, F. culmorum, F. moniliforme, F. poae*, and *Microdochium nivale*. The ITS sequences were determined and sequences were compared within each pathogen group the to locate divergences that might be useful to test in PCR to distinguish the different species and/or strains. The sequences of the ITS regions which were determined are shown as Sequence ID's 1–6, 47, 82–86, and 96 and also in FIGS. 1–3. From the identification of divergences, numerous, primers were synthesized and tested in PCR-amplification. Templates used for PCR-amplification testing were firstly purified pathogen DNA, and subsequently DNA isolated from infected host plant tissue. Thus, it was possible to identify pairs of primers that were diagnostic i.e. that identified one particular pathogen species or strain but not another species or strain of the same pathogen. Preferred primer combinations are able to distinguish between the different species or strains in infected host tissue, i.e. host tissue that has previously been infected with a specific pathogen species or strain.

This invention provides numerous primer combinations that fulfill this criterion for different Septoria, Mycosphaerella, Fusarium, and Microdochium species and different strains of Pseudocercosporella. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree C. to achieve good sensitivity and should be void of significant secondary structure and 3' overlaps between primer combinations. Primers generally have sequence identity with at least about 5–10 contiguous nucleotide bases of ITS 1 or ITS2. In preferred embodiments, primers are anywhere from about 5–30 nucleotide bases long.

The usefulness of cloned ITS sequences for the selection of primers for diagnostic purposes is largely due to their rapid evolutionary divergence. For example, W-type and R-type isolates of the pathogen *Pseudocercosporella herpotrichoides* have been found to have divergent ITS sequences from which diagnostic primers are developed. However, the rapid divergence within the ITS sequence is apparent from the observation that two different sequence variants of the W-type have been identified. The sequence identity within the W-type is 99.4%, whereas that between W and R-types is 98.6%, suggesting a closer evolutionary relationship between the two W variants than that found between the W and the R-types. This closer relationship is also apparent from their similar host pathogenicity of the two isolates with divergent ITS sequences.

In addition to developing primers from ITS-derived sequences for PCR diagnosis of fungal isolates, the invention also encompasses the identification of primers from RAPD primer libraries, which can distinguish between *Septoria nodorum* and *Septoria tritici* when used in PCR. The primers screened are commercially available and may be obtained from Operon Technologies Incorporated (Alameda, Calif.). In one example, screening on Septoria genomic DNA identified two primers that were able to detect only *S. tritici* and three that were able to detect only *S. nodorum*.

The present invention lends itself readily to the preparation of "kits" containing the elements necessary to carry out the process. Such a kit may comprise a carrier being compartmentalized to receive in close confinement therein one or more containers, such as tubes or vials. One of the containers may contain unlabeled or detectably labeled DNA primers. The labeled DNA primers may be present in lyophilized form, or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Fungal Isolates and Genomic DNA Extraction

Viable fungal isolates of *S. nodorum, S. tritici, S. passerini, S. glycines, Pseudocercosporella herpotrichoides, Pseudocercosporella aestiva, Mycosphaerella citri, Mycosphaerella graminicola, Mycosphaerella fijiensis* and *Mycosphaerella musicola* were obtained from the American Type Culture Collection. *Fusarium culmorum, Fusarium graminearum*, and *Fusarium poae* isolates were obtained from Dr. Paul Nelson from Penn State University. Isolates of *Michrodochium nivale* (syn. *Fusarium nivale*) were received from Novartis-Basel and an isolate of *Fusarium moniliforme* was received from Dr. Loral Castor. Dr. Bruce McDonald from Texas A&M University supplied genomic DNA from ten isolates of *S. nodorum* and nine isolates of *S. tritici*. Dr. Chris Caten of Birmingham University provided six isolates of *Septoria nodorum* purified fungal DNA. Purified genomic DNA from 12 isolates of *Pseudocercosporella herpotrichoides* was obtained from Dr. Paul Nicholson of the John Innes Centre, Norwich, UK. Six of these isolates are of the W-type; the other six isolates are of the R-type. These isolates were typed based on pathogenicity and RFLP studies. Andrea Johanson of the Natural Resources Institute supplied genomic DNA of six isolates of *M. musicola*, six isolates of *M. fijiensis* and a single isolate of *Mycosphaerella musae*. Purified genomic DNA from *Septoria avenae* f. sp. *triticea* ATCC#26380 was supplied by Dr. Peter Ueng from the USDA at Beltsville, Md. See Table 1 below for a complete listing of the fungal isolates used and their source.

TABLE 1

| | Source of Test Isolates | | |
|---|---|---|---|
| Isolate | Species | Origin | Source |
| ATCC#24425 | *S. nodorum* | Montana | ATCC[1] |
| XA1.1 | *S. nodorum* | Texas | B. McDonald[2] |
| Xa5A.2 | *S. nodorum* | Texas | B. McDonald |
| YA3.1 | *S. nodorum* | Texas | B. McDonald |

TABLE 1-continued Source of Test Isolates

| Isolate | Species | Origin | Source |
|---|---|---|---|
| XD2.1 | S. nodorum | Texas | B. McDonald |
| YB2.2 | S. nodorum | Texas | B. McDonald |
| 93HBh6a | S. nodorum | Oregon | B. McDonald |
| 93A3a | S. nodorum | Oregon | B. McDonald |
| 93AYa | S. nodorum | Oregon | B. McDonald |
| 93HBh8a | S. nodorum | Oregon | B. McDonald |
| 93C5a | S. nodorum | Oregon | B. McDonald |
| ATCC#26517 | S. tritici | Minnesota | ATCC |
| BS3 | S. nodorum | Ireland | C. Caten[3] |
| BS6 | S. nodorum | Ireland | C. Caten |
| BS175 | S. nodorum | England | C. Caten |
| BS425 | S. nodorum | England | C. Caten |
| alpha'5 | S. nodorum | France | C. Caten |
| m300 | S. nodorum | England | C. Caten |
| TKV2a | S. tritici | Turkey | B. McDonald |
| SYK2 | S. tritici | Syria | B. McDonald |
| ISZC36.2 | S. tritici | Israel | B. McDonald |
| CNRC4a.1 | S. tritici | Canada | B. McDonald |
| ALA1a | S. tritici | Algeria | B. McDonald |
| ETK1 | S. tritici | Ethiopia | B. McDonald |
| GEB2a.1 | S. tritici | Germany | B. McDonald |
| UK92D2 | S. tritici | United Kingdom | B. McDonald |
| DNB1a | S. tritici | Denmark | B. McDonald |
| ATCC#38699 | S. glycines | Illinois | ATCC |
| ATCC#22585 | S. passerini | Minnesota | ATCC |
| ATCC#42040 | P. herpotrichoides-wheat | | ATCC |
| ATCC#62012 | P. aestiva | Germany | ATCC |
| ATCC#60972 | P. herp. var. herp.-barley | Germany | ATCC |
| W1 | P. herpotrichoides | United Kingdom | P. Nicholson[4] |
| W2 | P. herpotrichoides | United Kingdom | P. Nicholson |
| W3 | P. herpotrichoides | United Kingdom | P. Nicholson |
| W4 | P. herpotrichoides | United Kingdom | P. Nicholson |
| W5 | P. herpotrichoides | New Zealand | P. Nicholson |
| W6 | P. herpotrichoides | Italy | P. Nicholson |
| R1 | P. herpotrichoides | Belgium | P. Nicholson |
| R2 | P. herpotrichoides | New Zealand | P. Nicholson |
| R3 | P. herpotrichoides | Germany | P. Nicholson |
| R4 | P. herpotrichoides | Sweden | P. Nicholson |
| R5 | P. herpotrichoides | United Kingdom | P. Nicholson |
| R6 | P. herpotrichoides | United Kingdom | P. Nicholson |
| ATCC#22116 | M. fijiensis | Philippines | ATCC |
| ATCC#22115 | M. musicola | Philippines | ATCC |
| ATCC#24046 | M. citri | Florida | ATCC |
| ATCC#62714 | M. graminicola | Montana | ATCC |
| PA92 | M. fijiensis | Panama | A. Johanson[5] |
| PNG291 | M. fijiensis | Papua New Guinea | A. Johanson |
| GH6-3 | M. fijiensis | Ghana | A. Johanson |
| TG120 | M. fijiensis | Tonga | A. Johanson |
| HSB4 | M. fijiensis | Honduras | A. Johanson |
| RT689 | M. fijiensis | Rarotonga (Cook Is.) | A. Johanson |
| CR548 | M. musicola | Costa Rica | A. Johanson |
| CM61 | M. musicola | Cameroon | A. Johanson |
| CU823 | M. musicola | Cuba | A. Johanson |
| MQ103 | M. musicola | Martinique | A. Johanson |
| C131 | M. musicola | Ivory Coast | A. Johanson |
| CB90 | M. musicola | Colombia | A. Johanson |
| BD1-4 | M. musae | Barbados | A. Johanson |
| ATCC#44234 | Ceratobasidium cereale | Netherlands | ATCC |
| ATCC#11404 | Drechslera sorokiniana | Minnesota | ATCC |
| R-5126 | F. culmorum | Minnesota | P. Nelson[6] |
| R-5106 | F. culmorum | Michigan | P. Nelson |
| R-5146 | F. culmorum | Finland | P. Nelson |
| R-8417 | F. graminearum | Italy | P. Nelson |
| R-8422 | F. graminearum | Canada | P. Nelson |
| R-8546 | F. graminearum | Bulgaria | P. Nelson |
| 4551 | F. moniliforme | Indiana | L. Castor[7] |
| 92 | M. nivale var. majus | — | Novartis Basel[8] |
| 93 | M. nivale var. majus | — | Novartis Basel |
| 69 | M. nivale | — | Novartis Basel |
| 72 | M. nivale | — | Novartis Basel |
| 520 | M. nivale | — | Novartis Basel |
| 18222 | M. nivale | Scotland | ATCC |
| ATCC#26380 | S. avenae f.sp. triticea | Minnesota | P. Ueng[9] |
| T-0427 | F. poae | Lancaster County, PA | P. Nelson |
| T-0534 | F. poae | Rock Springs, PA | P. Nelson |

TABLE 1-continued

Source of Test Isolates

| Isolate | Species | Origin | Source |
|---------|---------|--------|--------|
| T-0756 | F. poae | Unionville, PA | P. Nelson |
| 44643 | P. herpotrichoides W-type | Germany | ATCC |
| 308 | P. herpotrichoides R-type | — | Novartis Basel |

[1]American Type Culture Collection, Rockville, Maryland USA
[2]Dr. Bruce McDonald, Texas A & M University, USA
[3]Dr. Chris Caten, Birmingham University, UK
[4]Dr. Paul Nicholson, John Innes Centre, UK
[5]Dr. Andrea Johanson, Natural Resources Institute, UK
[6]Dr. Paul Nelson, Penn State University
[7]Dr. Loral Castor, Ciba Seeds Research, Bloomington, Illinois
[8]Novartis Crop Protection Limited, Basel, Switzerland
[9]Dr. Peter Ueng, USDA, Beltsville, Maryland Fungi were grown in 150 ml potato dextrose broth inoculated with mycelial fragments from PDA (Potato Dextrose Agar) cultures. Cultures were incubated on an orbital shaker at 28° C. for 7–11 days. Mycelia were pelleted by centrifugation and then ground in liquid nitrogen and total genomic DNA extracted using the protocol of Lee and Taylor (1990; In: *PCR Protocols: A Guide to Methods and Applications*; Eds.: Innes et al.; pages 282–287).

Eyespot-infected wheat stems were received from the stage 1c fungicide screening program of Ciba Basle. Eight day old wheat plants were infected with *P. herpotrichoides* by spraying a conidial suspension ($5\times10^5$ conidia/ml) in 0.2% Tween 20 on the base of the wheat stems. After inoculation, the plants were covered with plastic and incubated for one day at 20° C. and 95–100% relative humidity. The plants were transferred to a growth chamber where they were incubated for four weeks at 12° C. and 60% relative humidity. After this incubation, the plants were moved to a greenhouse and incubated at 18° C. and 60% relative humidity. Wheat plants infected with W-type *P. herpotrichoides* strain 311 were sampled at 8–9 weeks post-infection, while those infected with the R-type strain 308 pathogen were harvested at 9–10 weeks post-infection.

Example 2

Isolation of the Internal Transcribed Spacer (ITS) Regions

The approximately 550 bp internal transcribed spacer region fragments were PCR amplified from 25 ng of genomic DNA isolated from *S. nodorum* (ATCC#24425), *S. tritici* (ATCC#26517), *Pseudocercosporella herpotrichoides* isolates R1, R2, W2 and W5, *M. fijiensis* (ATCC#22115) and *M. musicola* (ATCC#22115) using 50 pmol of primers ITS1 (5'-TCCGTAGGTGAACCTGCGG-3'; SEQ ID NO: 38) and ITS4 (5'-TCCTCCGCTTATTGATATGC-3'; SEQ ID NO:41). PCRs were performed as described in EXAMPLE 4 except that reactions were done in 100 μl and annealing was done at of 50° C. The ITS fragments were purified by isopropanol precipitation according to Maniatis et al. (1982; *Molecular Cloning*; Eds.: Maniatis et al.; pages 461–462). The DNA was resuspended in 50 μl dH$_2$O and cloned using the Invitrogen Corporation's (San Diego, Calif.) TA Cloning Kit (part no. K2000-01) using the pCRII cloning vector. The DNA sequences of the ITS regions were determined by the dideoxy method using the Applied Biosystems (Foster City, Calif.) automated sequencer model 373A with the primers ITS1 (see sequence above), ITS2 (5'-GCTGCGTTCTTCATCGATGC-3'; SEQ ID NO:39), ITS4 (see sequence above) and the M13 universal -20 (5'-GTAAAACGACGGCCAGT-3'; SEQ ID NO:48) and Reverse (5'-AACAGCTATGACCATG-3'; SEQ ID NO:49) primers. The ITS primers ITS1 (SEQ ID NO:38), ITS2 (SEQ ID NO:39), ITS3 (SEQ ID NO:40), and ITS4 (SEQ ID NO:41) used for cloning the ITS regions are detailed in White et al. (1990; In: PCR Protocols; Eds.: Innes et al. pages 315–322).

In addition, the internal transcribed spacer regions were PCR amplified from 25 ng of genomic DNA from *S. avenae* f.sp. *triticea*; *M. nivale* isolates 72, 520, and 18222; *F. moniliforme* isolate #4551; *F. graminearum* isolates R-8417, R-8546 and R-8422; *F. culmorum* isolates R-5126, R-5106 and R-5146; and *F. poae* isolates T-0427, T-0534, and T-0756. PCR products were purified using Promega's Wizard DNA Clean-up kit (Madison, Wis.). PCR products from amplifications with *F. moniliforme* isolate #4551, *F. poae* isolates T-0427, T-0534 and T-0756 and *M. nivale* isolates 520, 72 and 18222 were cloned using the Invitrogen Corporation's (San Diego, Calif.) TA Cloning Kit (part no. K2000-01) using the PCR2.1 cloning vector. The DNA sequences of the ITS regions were determined as described above using the ITS1 (SEQ ID NO:38), ITS2 (SEQ ID NO:39), ITS3 (SEQ ID NO:40), ITS4 (SEQ ID NO:41), M13 universal -20 (SEQ ID NO:48), and Reverse (SEQ ID NO:49) primers. Sequencing reactions were combined with the three isolates of *F. culmorum*, *F. graminearum*, *M. nivale*, and *F. poae* to generate consensus ITS sequences for these fungi.

Example 3

DNA Extraction from Wheat and Banana Leaves

DNA is extracted from wheat leaves using a modified version of the Rapid DNA Extraction protocol from the MicroProbe Corporation's (Garden Grove, Calif.) IsoQuick Nucleic Acid Extraction Kit (cat# MXT-020-100). Typical yields are 5–10 μg of total DNA from 0.2 g of leaf tissue. Approximately 100 ng of total DNA are used in each PCR assay.

Modified Rapid DNA Extraction

Before using kit for the first time, the entire contents of Reagent 2A (20×Dye Concentrate) are added to Reagent 2 (Extraction Matrix).

(1) Approximately 0.2 g of leaf sample are added to a 1.5 ml eppendorf tube containing 50 μl sample buffer A and 50 μl #1 lysis solution. The leaf sample is ground with a Kontes pestle.

(2) Reagent 2 (Extraction Matrix) is shaken vigorously. 350 μl of reagent 2 are added to the sample lysate.

(3) 200 μl of Reagent 3 are added (Extraction Buffer) to the sample. The sample is vortexed 20 sec.

(4) Microcentrifugation at 12,000×g for 5 min.

(5) The aqueous phase (upper layer) is transferred to a new microcentrifuge tube.

This volume is typically about 200 μl.

(6) 0.1×the volume of the aqueous phase of Reagent 4 (Sodium Acetate) to the aqueous phase sample.

(7) An equal volume of isopropanol is added to the aqueous phase sample followed by vortexing.

(8) Microcentrifugation at 12,000×g for 10 min.

(9) The supernatant is discarded without disturbing the nucleic acid pellet. 0.5 ml of −20° C. 70% ethanol is added to the pellet. The tube is vortexed to mix.

(10) Microcentrifugation at 12,000×g for 5 min.

(11) The supernatant is discarded and the is allowed to dry.

(12) The nucleic acid pellet is dissolved in 50 μl Reagent 5 (RNase-free water).

DNA may also extracted from wheat using a bulk maceration method. The bulk maceration method is used to isolate DNA from several naturally infected wheat heads or stems from the field to optimize the field sampling method for high throughput analysis.

Bulk Maceration Method (1) Place the appropriate number of wheat heads or stems in a Bioreba (Reinach, Switzerland) heavy duty plastic bag (cat#490100). Weigh the plant tissue, plastic bag with leaves minus the tare (weight of the plastic bag).

(2) Add an equal volume (ml) of Muller Extraction Buffer (0.1% w/v Tween-80; 0.04M Tris-Cl, pH 7.7; 0.15M NaCl; 0.1% w/v BSA-Pentex fraction V; 0.01% w/v sodium azide; 200 mM EDTA) per weight (g) of wheat tissue. Macerate the tissue using a Bioreba Homex 6 homogenizer set at 70. Grind the leaves until the tissue is fibrous.

(3) Pool the extracts from multiple bags, if used, and vortex well. Aliquote the extraction juice into eppendorf tubes on ice.

(a) Boil 100 μl of the concentrated extract for 5 minutes.

(b) Place the boiled extract on ice.

(c) Make a 1:10 dilution by adding 10 μl from the boiled, concentrated extract to 90 μl of sterile dH$_2$O.

(d) Store the diluted extracts on ice until ready to use.

For the *P. herpotrichoides* PCR assay (see below), DNA is extracted from wheat stems using the protocol described by Klimyuk et al. (The Plant Journal 3(3): 493–494) with some modifications. A 2 cm wheat stem cut 0.5 cm above the basal culm is placed in 160 μl of 0.25M NaOH and ground with a Kontes pestle until completely macerated. The sample is boiled for 30 seconds. 160 μl of 0.25M HCl and 80 μl of 0.5M Tris-Cl, pH8.0/0.25% v/v Nonidet P-40 are added to the sample. The sample is boiled for an additional 2 minutes then placed in an ice water bath. 1 μl of extract is used in the PCR assay.

Example 4

Polymerase Chain Reaction Amplification

Polymerase chain reactions are performed with the GeneAmp Kit from Perkin-Elmer/Cetus (Norwalk, Conn.; part no. N808-0009) using 50 mM KCl, 2.5 mM MgCl$_2$, 10 mM Tris-HCl, pH8.3, containing 100 μM of each TTP, dATP, dCTP, and dGTP, 50 pM primer, 2.5 units of Taq polymerase and 25 ng of genomic DNA in a final volume of 50 μl. Reactions are run for 30 cycles of 15 s at 94° C., 15 s at 50° C., 60° C. or 70° C., and 45 s at 72° C. in a Perkin-Elmer/Cetus Model 9600 thermal cycler. The products are analyzed by loading 20 μl of each PCR sample on a 1.1–1.2% agarose gel and electrophoresing.

Example 5

Synthesis and Purification of Oligonucleotides

Oligonucleotides (primers) are synthesized, for example, on an Applied Biosystems 380A DNA synthesizer using B-cyanothyl-phosphoramidite chemistry, or by either Integrated DNA Technologies (Coralville, Iowa) or Midland Certified Reagent Company (Midland, Tex.).

Example 6

Selection of Species-Specific Primers

The sequences of the ITS regions of *S. nodorum, S. tritici, P. herpotrichoides* strains R and W, *M. fijiensis* and *M. musicola* are aligned (FIG. 1). The ITS sequences of *S. nodorum* and *S. avenae. triticea* are also aligned (FIG. 2). Additionally, an alignment is made of the ITS sequences from *F. graminearum, F. culmorum, F. monilifonne, F. poae* and *M. nivale* (FIG. 3). Oligonucleotide primers such as those shown below in Table 2 are synthesized according to Example 5 based on analysis of the aligned sequences. Primers are designed to regions containing the greatest differences in sequence among the fungal species. In addition, for the sequences shown in FIG. 3, primers are designed to regions of highest homology within the ITS regions of Fusarium. Furthermore, the published ribosomal gene-specific primers ITS1 (SEQ ID NO:38), ITS2 (SEQ ID NO:39), ITS3 (SEQ ID NO:40) and ITS4 (SEQ ID NO:41) (White et al., 1990; In: PCR Protocols; Eds.: Innes et al. Pages 315–322) are synthesized for testing in combination with the newly designed primers specific for the ITS regions to test for novel specificities.

TABLE 2

Primer Design for Fungal Detection

| Primer Template | Primer Name | Primer Sequence |
| --- | --- | --- |
| S. nodorum | JB433 | 5' ACACTCAGTAGTTTACTACT 3' (SEQ ID NO:7) |
| S. nodorum | JB434 | 5' TGTGCTGCGCTTCAATA 3' (SEQ ID NO:8) |
| S. nodorum | JB525 | 5' GCGACTTGTGCTGCGCTTCAATA 3' (SEQ ID NO:9) |
| S. nodorum | JB527 | 5' CATTACACTCAGTAGTTTACTACT 3' (SEQ ID NO:10) |
| S. tritici | JB445 | 5' CTGCGTCGGAGTTTACG 3' (SEQ ID NO:11) |
| S. tritici | JB446 | 5' CGAGGCTGGAGTGGTGT 3' (SEQ ID NO:12) |
| S. tritici | JB526 | 5' CCCAGCGAGGCTGGAGTGGTGT 3' (SEQ ID NO:13) |

TABLE 2-continued

Primer Design for Fungal Detection

| Primer Template | Primer Name | Primer Sequence |
|---|---|---|
| P. herp. | JB536 | 5' CTGGGGGCTACCCTACTTGGTAG 3' (SEQ ID NO: 14) |
| P. herp. | JB537 | 5' GGGGGCTACCCTACTTGGTAG 3' (SEQ ID NO:15) |
| P. herp. | JB538 | 5' ACTTGGTAGGGTTTAGAGTCGTCA 3' (SEQ ID NO:16) |
| P. herp. | JB539 | 5' CTTCGGTAAGGTTTAGAGTCGTCG 3' (SEQ ID NO:17) |
| P. herp. | JB540 | 5' GGGGGCCACCCTACTTCGGTAA 3' (SEQ ID NO:18) |
| P. herp. | JB541 | 5' CCACTGATTTTAGAGGCCGCGAG 3' (SEQ ID NO:19) |
| P. herp. | JB542 | 5' CCACTGATTTTAGAGGCCGCGAA 3' (SEQ ID NO:20) |
| P. herp. | JB543 | 5' CCTGTAAAAAATTGGGGGTTA 3' (SEQ ID NO:21) |
| P. herp. | JB544 | 5' CCTGTAAAAAATTGGGGGTTG 3' (SEQ ID NO:22) |
| M. fijiensis | JB547 | 5' ATTACCGAGTGAGGGCTCACGC 3' (SEQ ID NO:23) |
| M. fijiensis | JB548 | 5' GTTGCTTCGGGGGCGACCTG 3' (SEQ ID NO:24) |
| M. fijiensis | JB442 | 5' TCGGGGGCGACCTGCCG 3' (SEQ ID NO:25) |
| M. fijiensis | JB443 | 5' CCGGAGGCCGTCTA 3' (SEQ ID NO:26) |
| M. fijiensis | JB545 | 5' CCACAACGCTTAGAGACGGACAG 3' (SEQ ID NO:27) |
| M. fijiensis | JB546 | 5' CACCCGCACTCCGAAGCGAATT 3' (SEQ ID NO:28) |
| M. fijiensis | JB549 | 5' GATCCGAGGTCAACCTTTGAATAA 3' (SEQ ID NO:29) |
| M. fijiensis | JB444 | 5' GGTCAACCTTTGAATAA 3' (SEQ ID NO:30) |
| M. musicola | JB451 | 5' CCTTTGTGAACCACACCT 3' (SEQ ID NO:31) |
| M. musicola | JB440 | 5' CTGCCGGCGAACTT 3' (SEQ ID NO:32) |
| M. musicola | JB449 | 5' ACCCTGCCGGCGAACTT 3' (SEQ ID NO:33) |
| M. musicola | JB448 | 5' GCGACCCTGCCGGCGAAC 3' (SEQ ID NO:34) |
| M. musicola | JB441 | 5' TAGCCGGGAGACTTTGG 3' (SEQ ID NO:35) |
| M. musicola | JB450 | 5' TCTGCGTCGGAGTTCC 3' (SEQ ID NO:36) |
| M. musicola | JB452 | 5' CCGCGCTCCGGAGCGAAC 3' (SEQ ID NO:37) |
| 18S rDNA | ITS1 | 5' TCCGTAGGTGAACCTGCGG 3' (SEQ ID NO:38) |
| 5.8S rDNA | ITS2 | 5' GCTGCGTTCTTCATCGATGC 3' (SEQ ID NO:39) |
| 5.8S rDNA | ITS3 | 5' GCATCGATGAAGAACGCAGC 3' (SEQ ID NO:40) |
| 25S rDNA | ITS4 | 5' TCCTCCGCTTATTGATATGC 3' (SEQ ID NO:41) |
| S. nodorum | JB563 | 5' CTTGCCTGCCGGTTGGACAAATT 3' (SEQ ID NO:50) |
| S. nodorum | JB564 | 5' CTCAGTAGTTTACTACTGTAAAAGG 3' (SEQ ID NO:51) |
| S. nodorum | JB565 | 5' CTTCTGGACGCAAGTGTTTGTTAC 3' (SEQ ID NO:52) |
| Fusarium spp. | JB566 | 5' GTTTTTAGTGGAACTTCTGAGT 3' (SEQ ID NO:53) |
| Fusarium spp. | JB567 | 5' CGCAGGAACCCTAAACTCT 3' (SEQ ID NO:54) |
| Fusarium spp. | JB568 | 5' GCCCGCCGCAGG 3' (SEQ ID NO:55) |
| Fusarium spp. | JB569 | 5' RTWWTTWRTGGAMYYTCTGAGT 3' (SEQ ID NO:56) |
| Fusarium spp. | JB570 | 5' TATGTTGCCTCGGCGG 3' (SEQ ID NO:57) |
| Fusarium spp. | JB571 | 5' TAACGATATGTAAATTACTACGCT 3' (SEQ ID NO:58) |
| Fusarium spp. | JB572 | 5' AAGTTGGGGTTTAACGGC 3' (SEQ ID NO:59) |
| Fusarium spp. | JB573 | 5' AGCGAGCCCGCCAC 3' (SEQ ID NO:60) |
| Fusarium spp. | JB574 | 5' CCATTGTGAACGTTACCTATAC 3' (SEQ ID NO:61) |
| Fusarium spp. | JB575 | 5' CGACCAGAGCGAGATGTA 3' (SEQ ID NO:62) |
| Fusarium spp. | JB576 | 5' GTGAACATACCTTATGTTGCC 3' (SEQ ID NO:63) |
| Fusarium spp. | JB577 | 5' GTTGCCTCGGCGGATC 3' (SEQ ID NO:64) |
| Fusarium spp. | JB578 | 5' CCGCGACGATTACCAG 3' (SEQ ID NO:65) |
| Fusarium spp. | JB605 | 5' CCAAACCATGTGAACTTACC 3'(SEQ ID NO:87) |
| M. nivale | JB606 | 5' GGACTACCTAAACTCTGTT 3'(SEQ ID NO:88) |
| M. nivale | JB607 | 5' AGGGATCATTACCGAGTTT 3'(SEQ ID NO:89) |
| M. nivale | JB609 | 5' TCCGGCTTGCAGAAGCGAG 3'(SEQ ID NO:90) |
| M. nivale | JB610 | 5' GAAGGGTGCGGTTTATGGCT 3'(SEQ ID NO:91) |
| M. nivale | JB611 | 5' GCCACCGCCGGTGGAC 3'(SEQ ID NO:92) |
| M. nivale | JB612 | 5' GGTGCTGTCTCTCGGGAC 3'(SEQ ID NO:93) |
| M. nivale | JB613 | 5' AGTCAATCTGAATCAAACTAAG 3'(SEQ ID NO:94) |
| M. nivale | JB614 | 5' CTAAACTCTGTTAATTTTTGTCAA 3'(SEQ ID NO:95) |

NOTE: Fusarium spp. includes *F. graminearum*, *F. culmorum*, *F. moniliforme* and *Michrodochium nivale* (syn. *F. nivale*).

Example 7

Selection of Random Amplified Polymorphic DNA (RAPD) primers

Two RAPD primer libraries (kits B and E) of twenty oligonucleotides each are purchased from Operon Technologies Incorporated (Alameda, Calif.). The primers are tested for their ability to differentiate purified genomic DNA of *S. nodorum*, *S. tritici*, *M. fijiensis* and *M. musicola*. The PCR conditions are essentially the same as described in Example 4 except the number of PCR cycles is increased to 35, the annealing temperature is 30° C. and only 5 picamoles of each primer are used. In a representative experiment, five RAPD primers were identified that differentiated purified genomic DNA of *S. nodorum*, *S. tritici*, *M. fijiensis* and *M. musicola*. Primers OPB-12 and OPE-6 produced a single fragment when amplified with *S. tritici* genomic DNA. Primers OPE-12, OPB-19 and OPE-15 produced single fragments from *S. nodorum* genomic DNA. Primers OPB-12 and OPE-6 did not produce any amplification products from *S. nodorum* *M. fijiensis* and *M. musicola* genomic DNA. Primers OPE-12, OPB-19 and OPE-15 did not amplify any fragments from genomic *S. tritici*, *M. fijiensis* or *M. musicola* DNA.

TABLE 3

RAPD Primers for Septoria Diagnosis

| Source of template DNA | Primer | Sequence of primer | Approximate size of amplified fragment |
|---|---|---|---|
| S. tritici | OPB-12 | 5'-CCTTGACGCA-3' (SEQ ID NO: 42) | 1.3 kb |
| S. tritici | OPE-6 | 5'-AAGACCCCTC-3' (SEQ ID NO: 43) | 1.0 kb |
| S. nodorum | OPE-12 | 5'-TTATCGCCCC-3' (SEQ ID NO: 44) | 2.2 kb |
| S. nodorum | OPB-19 | 5'-ACCCCCGAAG-3' (SEQ ID NO: 45) | 1.1 kb |
| S. nodorum | OPE-15 | 5'-ACGCACAACC-3' (SEQ ID NO: 46) | 1.3 kb |

Example 8

Determination of Primer Specificity to Purified Fungal Genomic DNA

PCRs are performed according to Example 4 using different primer combinations in an attempt to amplify a single species-specific fragment. Species-specific PCR amplification products are produced from primers designed from the sequences of the ITS regions between the 18S and 25S ribosomal DNA subunits of each fungal strain of interest.

TABLE 4

ITS-Derived Diagnostic PCR Primers

| Source of template DNA | 5'Primer | 3'Primer | Approximate size of amplified fragment |
|---|---|---|---|
| *Septoria nodorum* | | | |
| | JB433 (SEQ ID NO:7) | JB434 (SEQ ID NO:8) | 448 bp |
| | JB433 (SEQ ID NO:7) | ITS4 (SEQ ID NO:41)(JB415) | 553 bp |
| | ITS1 (SEQ ID NO:38)(JB410) | JB434 (SEQ ID NO:8) | 478 bp |
| | ITS3 (SEQ ID NO:40)(JB414) | JB434 (SEQ ID NO:8) | 232 bp* |
| | JB527 (SEQ ID NO:10) | JB525 (SEQ ID NO:9) | 458 bp |
| | JB564 (SEQ ID NO:51) | JB565 (SEQ ID NO:52) | 480 bp |
| | JB563 (SEQ ID NO:50) | JB565 (SEQ ID NO:52) | 368 bp |
| *Septoria tritici* | | | |
| | JB445 (SEQ ID NO:11) | IT54 (SEQ ID NO:41)(JB415) | 407 bp |
| | ITS1 (SEQ ID NO:38)(JB410) | JB446 (SEQ ID NO:12) | 345 bp |
| | ITS3 (SEQ ID NO:40)(JB414) | JB446 (SEQ ID NO:12) | 143 bp* |
| | JB445 (SEQ ID NO: 11) | JB446 (SEQ ID NO: 12) | 204 bp |
| *M. fijiensis* | | | |
| | JB443 (SEQ ID NO:26) | ITS4 (SEQ ID NO:41)(JB415) | 418 bp |
| | ITS1 (SEQ ID NO:38)(JB410) | JB444 (SEQ ID NO:30) | 482 bp |
| | JB443 (SEQ ID NO:26) | JB444 (SEQ ID NO:30) | 366 bp* |
| | ITS3 (SEQ ID NO:40)(JB414) | JB444 (SEQ ID NO:30) | 281 bp* |
| | ITS1 (SEQ ID NO:38)(JB410) | JB549 (SEQ ID NO:29) | 489 bp |
| *M. musicola* | | | |
| | JB449 (SEQ ID NO:33) | ITS4 (SEQ ID NO:41)(JB415) | 430 bp |
| | JB448 (SEQ ID NO:34) | ITS4 (SEQ ID NO:41)(JB415) | 449 bp* |
| | JB448 (SEQ ID NO:34) | ITS2 (SEQ ID NO:39)(JB411) | 138 bp* |
| | JB450 (SEQ ID NO:36) | ITS4 (SEQ ID NO:41)(JB415) | 390 bp* |
| *P. herpotrichoides* | | | |
| | JB536 (SEQ ID NO:14) | JB541 (SEQ ID NO:19) | 415 bp+ |
| | JB536 (SEQ ID NO:14) | JB543 (SEQ ID NO:21) | 502 bp+ |
| | JB537 (SEQ ID NO:15) | JB541 (SEQ ID NO:19) | 413 bp+ |
| | JB537 (SEQ ID NO:15) | JB543 (SEQ ID NO:21) | 500 bp+ |
| | JB538 (SEQ ID NO:16) | JB541 (SEQ ID NO:19) | 401 bp+ |
| | JB538 (SEQ ID NO:16) | JB543 (SEQ ID NO:21) | 488 bp+ |
| | JB536 (SEQ ID NO:14) | ITS4 (SEQ ID NO:41)(JB415) | 560 bp+ |
| | JB537 (SEQ ID NO:15) | ITS4 (SEQ ID NO:41)(JB415) | 558 bp+ |
| | JB538 (SEQ ID NO:16) | ITS4 (SEQ ID NO:41)(JB415) | 546 bp+ |
| | ITS1 (SEQ ID NO:38)(JB410) | JB541 (SEQ ID NO:19) | 482 bp+ |
| | ITS1 (SEQ ID NO:38)(JB410) | JB543 (SEQ ID NO:21) | 569 bp+ |
| | ITS1 (SEQ ID NO:38)(JB410) | JB542 (SEQ ID NO:20) | 482 bp+ |
| | ITS1 (SEQ ID NO:38)(JB410) | JB544 (SEQ ID NO:22) | 569 bp++ |
| | JB540 (SEQ ID NO: 18) | ITS4 (SEQ ID NO:41)(JB415) | 558 bp++ |
| | JB539 (SEQ ID NO:17) | ITS4 (SEQ ID NO:41)(JB415) | 545 bp++ |

TABLE 4-continued

ITS-Derived Diagnostic PCR Primers

| Source of template DNA | 5'Primer | 3'Primer | Approximate size of amplified fragment |
|---|---|---|---|
| | JB540 (SEQ ID NO:18) | JB542 (SEQ ID NO:20) | 413 bp++ |
| | JB540 (SEQ ID NO:18) | JB544 (SEQ ID NO:22) | 500 bp++ |
| | JB539 (SEQ ID NO:17) | JB542 (SEQ ID NO:20) | 400 bp++ |
| | JB539 (SEQ ID NO:17) | JB544 (SEQ ID NO:22) | 487 bp++ |
| Fusarium spp. | | | |
| | JB566 (SEQ ID NO:53) | ITS4 (SEQ ID NO:41)(JB415) | 430 bp[1] |
| | JB566 (SEQ ID NO:53) | JB572 (SEQ ID NO:59) | 346 bp[1] |
| | JB569 (SEQ ID NO:56) | ITS4 (SEQ ID NO:41)(JB415) | 430 bp[1] |
| | JB569 (SEQ ID NO:56) | JB572 (SEQ ID NO:59) | 346 bp[1] |
| | ITS1 (SEQ ID NO:38)(JB410) | JB572 (SEQ ID NO:59) | 485 bp[1] |
| | JB566 (SEQ ID NO:53) | JB571 (SEQ ID NO:58) | 308 bp[2] |
| | JB569 (SEQ ID NO:56) | JB571 (SEQ ID NO:58) | 308 bp[2] |
| | JB570 (SEQ ID NO:57) | ITS4 (SEQ ID NO:41)(JB415) | 501 bp[2] |
| | JB570 (SEQ ID NO:57) | JB571 (SEQ ID NO:58) | 379 bp[2] |
| | JB570 (SEQ ID NO:57) | JB578 (SEQ ID NO:65) | 395 bp[2] |
| | JB567 (SEQ ID NO:54) | ITS4 (SEQ ID NO:41)(JB415) | 450 bp[2] |
| | JB567 (SEQ ID NO:54) | JB571 (SEQ ID NO:58) | 328 bp[2] |
| | JB567 (SEQ ID NO:54) | JB572 (SEQ ID NO:59) | 366 bp[2] |
| | JB567 (SEQ ID NO:54) | JB578 (SEQ ID NO:65) | 344 bp[2] |
| | JB568 (SEQ ID NO:55) | ITS4 (SEQ ID NO:41)(JB415) | 459 bp[2] |
| | JB568 (SEQ ID NO:55) | JB571 (SEQ ID NO:58) | 337 bp[2] |
| | JB568 (SEQ ID NO:55) | JB572 (SEQ ID NO:59) | 375 bp[2] |
| | JB576 (SEQ ID NO:63) | ITS4 (SEQ ID NO:41)(JB415) | 510 bp[2] |
| | JB576 (SEQ ID NO:63) | JB578 (SEQ ID NO:65) | 404 bp[2] |
| | JB577 (SEQ ID NO:64) | ITS54 (SEQ ID NO:41)(JB415) | 495 bp[2] |
| | JB577 (SEQ ID NO:64) | JB571 (SEQ ID NO:58) | 373 bp[2] |
| | JB577 (SEQ ID NO:64) | JB578 (SEQ ID NO:65) | 389 bp[2] |
| | ITS1 (SEQ ID NO:38)(JB410) | JB571 (SEQ ID NO:58) | 447 bp[2] |
| | ITS1 (SEQ ID NO:38)(JB410) | JB578 (SEQ ID NO:65) | 463 bp[2] |
| | ITS1 (SEQ ID NO:38)(JB410) | JB575 (SEQ ID NO:62) | 479 bp[2] |
| | JB605 (SEQ ID NO:87) | ITS4 (SEQ ID NO:41) | 509 bp[3] |
| | JB605 (SEQ ID NO:87) | JB578 (SEQ ID NO:65) | 417 bp[4] |
| | JB605 (SEQ ID NO:87) | JB572 (SEQ ID NO:59) | 440 bp[5] |
| | JB605 (SEQ ID NO:87) | JB571 (SEQ ID NO:58) | 400 bp[5] |
| M. nivale | | | |
| | JB569 (SEQ ID NO:56) | JB575 (SEQ ID NO:62) | 340 bp |
| | JB567 (SEQ ID NO:54) | JB575 (SEQ ID NO:62) | 360 bp |
| | JB574 (SEQ ID NO:61) | ITS4 (SEQ ID NO:41)(JB415) | 520 bp |
| | JB574 (SEQ ID NO:61) | JB572 (SEQ ID NO:59) | 436 bp |
| | JB612 (SEQ ID NO:93) | ITS4 (SEQ ID NO:41) | 472 bp |
| | JB613 (SEQ ID NO:94) | JB610 (SEQ ID NO:91) | 337 bp |
| | JB614 (SEQ ID NO:95) | JB610 (SEQ ID NO:91) | 355 bp |
| | JB613 (SEQ ID NO:94) | ITS4 (SEQ ID NO:41) | 413 bp |
| | JB611 (SEQ ID NO:92) | JB609 (SEQ ID NO:90) | 346 bp |
| | JB611 (SEQ ID NO:92) | ITS4 (SEQ ID NO:41) | 450 bp |
| | ITS1 (SEQ ID NO:38) | JB609 (SEQ ID NO:90) | 452 bp |
| | ITS1 (SEQ ID NO:38) | JB610 (SEQ ID NO:91) | 480 bp |
| | JB605 (SEQ ID NO:87) | JB610 (SEQ ID NO:91) | 433 bp |
| | JB606 (SEQ ID NO:88) | JB610 (SEQ ID NO:91) | 362 bp |
| | JB607 (SEQ ID NO:89) | JB610 (SEQ ID NO:91) | 460 bp |

*Primer combination amplified some fragments by false priming but none were the size of the desired fragment.
+Primers amplified the correct size fragment from both R-type and W-type of *Pseudocercosporella herpotrichoides*.
++Primer combination amplified the correct size fragment from the R-type of *P. herpotrichoides* only.
[1]Primer combination amplified the correct size fragment from *F. graminearum*, *F. culmorum*, *F. moniliforme* and *M. nivale*.
[2]Primer combination amplified the correct size fragment from *F. graminearum*, *F. culmorum* and *F. moniliforme*.
[3]Primer combination amplified the correct size fragment from *M. nivale* and *F. graminearum*, *F. culmorum*, *F. avenaceum*, *F. poae*, and *F. moniliforme*.
[4]Primer combination amplified the correct size fragment from *F. graminearum*, *F. culmorum*, *F. roseum*, *F. poae*, and *F. moniliforme*.
[5]Primer combination amplified the correct size fragment from *F. graminearum* and *F. culmorum*.

Example 9
Determination of Primer Specificity to Plant Tissue Infected with Fungi and Cross-Reactivity With Other Fungal Pathogens Total genomic DNA is isolated from healthy wheat leaves, wheat leaves infected with *S. nodorum*, wheat leaves infected with *S. tritici* and wheat leaves infected with both *S. nodorum* and *S. tritici* using the protocol described in Example 3. PCRs are performed as described in Example 4 testing the primer combinations listed in Example 8 against DNA from the wheat leaves. The results of representative experiments are as follows:

*S. tritici*-specific primer combination JB446 (SEQ ID NO:12) and ITS1 (SEQ ID NO:38)(JB410) amplified a 345 bp fragment from purified genomic DNA of all the *S. tritici* isolates listed in Table 1, from *S. tritici*-infected wheat leaf tissue and from a wheat leaf sample infected with both *S. tritici* and *S. nodorum*. This primer combination did not amplify a diagnostic fragment from healthy wheat leaf tissue nor from *S. nodorum*-infected wheat tissue. Similarly, *S. tritici*-specific primer combination JB445 (SEQ ID NO:11) and ITS4 (SEQ ID NO:41)(JB415) amplified a 407 bp fragment from the same tissues as primer combination JB446 (SEQ ID NO:12) and ITSI (SEQ ID NO:38)(JB410), and was also diagnostic. There was no cross-reactivity with purified genomic DNA of *S. nodorum, S. glycines* or *S. passerini*. None of these other fungal species produced an amplification product with the *S. tritici*-specific Similarly, diagnostic results were obtained with *S. nodorum*-specific primer combination JB433 (SEQ ID NO:7) and JB434 (SEQ ID NO:8). This primer combination amplified a 448 bp fragment from *S. nodorum*-infected wheat tissue, from a wheat leaf sample infested with both *S. nodorum* and *S. tritici*, as well as from purified genomic DNA of all the *S. nodorum* isolates listed in Table 1. This primer combination did not amplify any fragments from healthy wheat tissue, from *S. tritici*-infected wheat tissue or from purified genomic DNA of *S. tritici*. *S. nodorum*-specific primer combination JB527 (SEQ ID NO:10) and JB525 (SEQ ID NO:9) amplified a 458 bp fragment from the same genomic DNAs and wheat tissues as primer combination JB433 (SEQ ID NO:7) and JB434 (SEQ ID NO:8). *S. tritici, S. glycines* and *S. passerini* did not produce any amplification products when assayed with the either *S. nodorum*-specific primer combination JB433 (SEQ ID NO:7) and JB434 (SEQ ID NO:8) or JB527 (SEQ ID NO:10) and JB525 (SEQ ID NO:9).

The *P. herpotrichoides*-specific primer combinations listed in EXAMPLE 8 are PCR tested against the extracts from wheat stems as obtained in Example 3. PCRs are performed as described in Example 4 with the following changes: 35 cycles are run of 94° C. for 15 sec and 70° C. for 45 sec, 1.5–2.5 mM MgCl2 and 200 μM of each dNTP is used. 1 μl of wheat extract is used in each PCR. The results of representative experiments are as follows:

Primer combination JB537 (SEQ ID NO:15) and JB541 (SEQ ID NO:19) amplified a 413 bp fragment from wheat extract infected with the W-type pathotype of *P. herpotrichoides*. No amplification products were produced from amplification with healthy wheat extract nor from wheat extract infected with the R-type pathotype of *P. herpotrichoides*. This primer combination produced a 413 bp fragment from the W-type *P. herpotrichoides* isolates only when tested against the *P. herpotrichoides* isolates and the following cereal pathogens: *P. aestiva, C. cereale, P. sorokiniana, S. tritici* and *S. nodorum*.

Primer combination JB539 (SEQ ID NO:17) and JB544 (SEQ ID NO:22) amplified a 487 bp fragment, and primer combination JB540 (SEQ ID NO:18) and JB542 (SEQ ID NO:20) amplified a 413 bp fragment from R-type infected wheat, but not from healthy wheat or from W-type infected wheat. Primer combination JB539 (SEQ ID NO:17) and JB544 (SEQ ID NO:22) amplified a 487 bp fragment from the R-type *P. herpotrichoides* isolate only when tested against the same DNAs. Primer combination JB540 (SEQ ID NO:18) and JB542 (SEQ ID NO:20) likewise produced a 413 bp fragment from the R-type *P. herpotrichoides* isolate only when tested against the same DNAs.

Total genomic DNA is isolated from healthy banana leaves and from banana leaves infected with *M. fijiensis* using the protocol described in Example 3. PCRs are performed as described in Example 4 testing the *M. fijiensis* primer combinations listed in Example 8 against DNA from the banana leaves. The results of representative experiments are as follows:

*M. fijiensis*-specific primer combination JB 549 (SEQ ID NO:29) and ITS1 (SEQ ID NO:38)(JB410) amplified a 489 bp fragment from purified *M. fijiensis* DNA and from *M. fijiensis*-infected banana leaf tissue. This primer combination did not amplify a diagnostic fragment from healthy banana leaf tissue. *M. fijiensis*-specific primer combinations JB443 (SEQ ID NO:26)/ITS4 (SEQ ID NO:41)(JB415) and ITS1 (SEQ ID NO:38)(JB410)/JB444 (SEQ ID NO:30) amplified a 418 bp fragment and a 482 bp fragment, respectively, from the same genomic DNA and banana leaf tissue as the JB549 (SEQ ID NO:29) and ITS1 (SEQ ID NO:38)(JB410) primer combination.

Total genomic DNA is isolated as described in Example 3 from healthy wheat heads and from wheat heads inoculated with either *M. nivale, F. graminearum, F. culmorum* or *F. avenaceum*. PCRs are performed as described in Example 4 testing primer combinations such as those listed in Table 3 against DNA from the wheat tissue. Purified fungal genomic DNAs are obtained as described in Example 1 and PCR assayed as described in Example 4 using the diagnostic primers. Other fungal DNA species and isolates are tested for the ability of the diagnostic primers to cross-react therewith. The results of representative experiments as follows:

*M. nivale*-specific primer combination JB612 (SEQ ID NO:93) and ITS4 (SEQ ID NO: 41) amplified a 472 bp fragment from DNA from all of the *M. nivale* isolates listed in Table 1 and from *M. nivale*-infected wheat tissue. This primer combinaton did not amplify a diagnostic fragment from healthy wheat tissue or from purified genomic DNA from *F. graminearum, F. culmorum, F. avenaceum, F. poae* or *F. moniliforme*. This primer combination also did not amplify a diagnostic fragment from purified genomic DNA isolated from the following common cereal pathogens: *P. herpotrichoides* R- and W-pathotypes. *C. cereale, D. sorokiniana, C. herbarum, S. glycines, S. tritici, C. arachidicola, S. nodorum, R. solani* and *S. avenae* f.sp. *triticea*. Similar diagnostic results were obtained with *M. nivale*-specific primer combination JB613 (SEQ ID NO:94) and JB610 (SEQ ID NO:91).

Primer combination JB613 (SEQ ID NO:94) and ITS4 (SEQ ID NO:41) amplified a 413 bp fragment, and primer combination JB614 (SEQ ID NO:95) and ITS4 (SEQ ID NO:41) amplified a 431 bp fragment from DNA from *M. nivale* isolate #520 and from wheat infected with *M. nivale*. These primer combinations did not amplify any fragments from healthy wheat tissue, nor from DNA from *F. graminearum* isolate #R-8422 and *F. culmorum* isolate #R-5391.

The remaining *M. nivale*-specific primer combinations listed in Table 3 amplified a PCR fragment from DNA from *M. nivale* isolate #520 but not from DNA from *F. graminearum* isolate #R-8422 nor *F. culmorum* isolate #R-5391.

Primer combination JB605 (SEQ ID NO:87) and ITS4 (SEQ ID NO:41) amplified a 509 bp fragment from DNA from all of the *M. nivale* isolate listed in Table 1. This primer combination also amplified a 509 bp fragment from DNA from all of the *F. graminearum, F. culmorum, F. avenaceum, F. poae* and *F. moniliforme* isolates listed in Table 1. This primer combination did not amplify a diagnostic fragment from purified genomic DNA isolated from the following cereal pathogens: *P. herpotrichoides* R- and W-pathotypes, *C. cereale, D. sorokiniana, C. herbarum, S. glycines, S. tritici, C. arachidicola, S. nodorum, R. solani* and *S. avenae* f.sp. *triticea*. Primer combination JB605 (SEQ ID NO:87) and ITS4 (SEQ ID NO:41) also amplified a diagnostic fragment from wheat infected with Fusarium spp. but not from healthy wheat.

Primer combinations JB605 (SEQ ID NO:87) and JB571 (SEQ ID NO:58); JB605 (SEQ ID NO:87) and JB572 (SEQ ID NO:59); and JB605 (SEQ ID NO:87) and JB578 (SEQ ID NO:65) amplified 400 bp, 440 bp and 417 bp fragments, respectively, from DNA from *F. graminearum* isolate #R-8422 and *F. culmorum* isolate #R-5391, but not from *M. nivale* isolate #520. In addition, primer combination JB605 (SEQ ID NO:87) and JB578 (SEQ ID NO:65) amplified a diagnostic fragment from all of the *F. graminearum, F. moniliforme, F. roseum, F. poae* and *F. culmorum* isolates listed in Table 1; however, this primer combination did not amplify from any of the *F. avenaceum* isolates nor *M. nivale* isolates listed in Table 1. Primer combinations JB605 (SEQ ID NO:87) and JB571 (SEQ ID NO:58); JB605 (SEQ ID NO:87) and JB572 (SEQ ID NO:59); and JB605 (SEQ ID NO:87) and JB578 (SEQ ID NO:65) did not amplify a diagnostic fragment from healthy wheat or from purified genomic DNA isolated from the cereal pathogens *P. herpotrichoides* R- and W-pathotypes, *C. cereale, D. sorokiniana, C. herbarum, S. glycines, S. tritici, C. arachidicola, S. nodorum, R. solani* and *S. avenae* f.sp. *triticea*.

Example 10

Incorporation of Diagnostic Assays into a Quantitative Colormetric Assay Format

A colormetric assay is performed according to Nikiforov et al. (PCR Methods and Applications 3: 285–291) with the following changes:

1) 30 μl of the R-type PCR product and 3M NaCl/20 mM EDTA mixture are added to the capture primer well. 50 μl of the W-type PCR product and 3M NaCl/20 mM EDTA mixture are used in the hybridization reaction.

2) The exonuclease treatment and hybridization reaction are incubated at 37° C.

3) A 1:1000 dilution of anti-biotin horseradish peroxidase (HRP) monoclonal antibody is used.

4) After a 2 min. incubation with the O-phenylenediamine dihydrochloride (OPD) substrate, 50 μl of 3N HCl are added to each assay well. 96-well plates are read at 492 nm and referenced at 570 nm using a conventional ELISA plate reader.

The primers listed in Table 5 are synthesized as described in Example 5 for testing as capture primers for the colormetric assay.

TABLE 5

Capture Primer Design for Colormetric Assay

| Primer Name | Primer Template | Primer Sequence |
|---|---|---|
| ITS2 | 5.8S rDNA | 5' GCTGCGTTCTTCATCGATGC 3' (SEQ ID NO:39) |
| JB541 | W-type *P. herp.* | 5' CCACTGATTTTAGAGGCCGCGAG 3'(SEQ ID NO:19) |
| JB542 | R-type *P. herp.* | 5' CCACTGATTTTAGAGGCCGCGAA 3'(SEQ ID NO:20) |
| JB538' | W-type *P. herp.* | 5' TGACGACTCTAAACCCTACCA 3' (SEQ ID NO:66) |
| JB539' | R-type *P. herp.* | 5' CGACGACTCTAAACCTTACCG 3' (SEQ ID NO:67) |
| W130 | W-type *P. herp.* | 5' ATTCAAGGGTGGAGGTCTGA 3' (SEQ ID NO:68) |
| R130 | R-type *P. herp.* | 5' ATTCAAGGGTGGAGGTCTGG 3' (SEQ ID NO:69) |
| JB538' 15 | W-type *P. herp.* | 5' CTCTAAACCCTACCA 3' (SEQ ID NO:70) |
| JB539' 15 | R-type *P. herp.* | 5' CTCTAAACCTTACCG 3' (SEQ ID NO:71) |
| JB553 | R & W types | 5' GTGGTCCTCTGGCAG 3' (SEQ ID NO:72) |
| JB554 | R & W types | 5' CTCAACAGCCGAAGC 3' (SEQ ID NO:73) |
| JB555 | W-type *P. herp.* | 5' GGGTGGAGGTCTGA 3' (SEQ ID NO:74) |
| JB556 | R-type *P. herp.* | 5' GGTGGAGGTCTGG 3' (SEQ ID NO:75) |
| JB561 | R-type *P. herp.* | 5' TGGAGGTCTGGACCA 3' (SEQ ID NO:76) |
| JB562 | W-type *P. herp.* | 5' TGGAGGTCTGAACCA 3' (SEQ ID NO:77) |
| JB559 | W-type *P. herp.* | 5' AGGGTGGAGGTCTGA 3' (SEQ ID NO:78) |
| JB560 | R-type *P. herp.* | 5' AGGGTGGAGGTCTGG 3' (SEQ ID NO:79) |
| JB557 | W-type *P. heip.* | 5' TTCTCCGAGAGGCCT 3' (SEQ ID NO:80) |
| JB558 | R-type *P. herp.* | 5' TTCTCCGAGAGGCCC 3' (SEQ ID NO:81) |

In a representative experiment, the *S. nodorum* diagnostic primers JB527 (SEQ ID NO:10) and JB525 (SEQ ID NO:9) were integrated into the quantitative colormetric assay format. The primer JB527 (SEQ ID NO:10) was synthesized by Midland Certified Reagent Company (Midland, Tex.) to contain a biotin label and the 5' end to contain four internucleotidic phosphorothioate bonds. PCR amplification as described in Example 4 using the modified JB527 (SEQ ID NO:10) and JB525 (SEQ ID NO:9) primers from healthy, low, medium, and highly *S. nodorum*-infected wheat produced no, low, medium and high $A_{492}$ values, respectively, when assayed colormetrically using the ITS2 (SEQ ID NO:39) primer as the PCR product capture primer.

The *P. herpotrichoides* R-type specific 5' primers, JB539 (SEQ ID NO:17) and JB540 (SEQ ID NO:18), and the *P. herpotrichoides* W-type specific 5' primer, JB537 (SEQ ID NO:15), were also modified to contain a biotin label and four internucleotidic phosphorothioate bonds. A colormetric version of the *P. herpotrichoides* R-type PCR assay was developed using the modified JB540 (SEQ ID NO:18) primer, JB542 (SEQ ID NO:20) primer and the capture primer JB539'15. The products produced from amplification from R-type infected wheat and from R-type genomic DNA using the modified JB540 (SEQ ID NO:18) primer and JB542 (SEQ ID NO:20) primer produced positive colormetric values when assayed colormetrically. Positive colormetric values were also obtained by colorimetric analysis of the PCR products from amplification using the modified JB537 (SEQ ID NO:15) primer and W-type specific primer JB541 (SEQ ID NO:19) with W-type infected wheat and W-type genomic DNA when JB538'15 was used as the capture primer. Furthermore, the intensity of the colorimetric signal corresponded to the fragment intensity of the PCR product as visualized on an agarose gel.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

DEPOSITS

The following deposits were made on Mar. 28, 1994, at Agricultural Research Service, Patent Culture Collection (NRRL), Northern Regional Research Center, 1815 North University Street, Peoria, Ill. 61604, U.S.A.:

1. HB101 DH5d (pCRW2-1; SEQ ID NO: 3) Accession No. NRRL B 21231
2. HB101 DH5d (pCRW5-1; SEQ ID NO: 47) Accession No. NRRL B-21232
3. *E. coli* DH5d (pCRSTRIT1; SEQ ID NO: 1) Accession No. NRRL B-21233
4. *E. coli* DH5d (pCRR1-21; SEQ ID NO: 4) Accession No. NRRL B-21234
5. *E. coli* DH5d (pCRSNOD31; SEQ ID NO: 2) Accession No. NRRL B-21235

SEQUENCE LISTING ( 1 ) GENERAL INFORMATION:

( i i i ) NUMBER OF SEQUENCES: 96

( 2 ) INFORMATION FOR SEQ ID NO:1:

( i ) SEQUENCE CHARACTERISTICS:
        ( A ) LENGTH: 548 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Septoria tritici ( i x ) FEATURE:
        ( A ) NAME/KEY: misc_feature
        ( B ) LOCATION: 1..30
        ( D ) OTHER INFORMATION: /note= "3'end of small subunit rRNA gene"

( i x ) FEATURE:
        ( A ) NAME/KEY: misc_feature
        ( B ) LOCATION: 31..172
        ( D ) OTHER INFORMATION: /note= "ITS 1"

( i x ) FEATURE:
        ( A ) NAME/KEY: misc_feature
        ( B ) LOCATION: 173..328
        ( D ) OTHER INFORMATION: /note= "5.8S rRNA gene"

( i x ) FEATURE:
        ( A ) NAME/KEY: misc_feature
        ( B ) LOCATION: 329..491
        ( D ) OTHER INFORMATION: /note= "ITS 2"

( i x ) FEATURE:
        ( A ) NAME/KEY: misc_feature
        ( B ) LOCATION: 492..548
        ( D ) OTHER INFORMATION: /note= "5'end of large subunit rRNA gene"

( x i ) SEQUENCE DESCRIPTION: SEQ ID NO:1:

```
TCCGTAGGTG AACCTGCGGA GGGATCATTA CCGAGCGAGG GCCTCCGGGT CCGACCTCCA      60

ACCCTTTGTG AACACATCCC GTTGCTTCGG GGGCGACCCT GCCGGCGCC  CCCGGAGGAC     120

CACCAAAAAA CACTGCATCT CTGCGTCGGA GTTACGAGT  AAATCGAAAC AAAACTTTCA     180

ACAACGGATC TCTTGGTTCT GGCATCGATG AAGAACGCAG CGAAATGCGA TAAGTAATGT     240
```

-continued

| | | | | | |
|---|---|---|---|---|---|
| GAATTGCAGA | ATTCAGTGAA | TCATCGAATC | TTTGAACGCA | CATTGCGCCC | CCTGGTATTC | 300 |
| CGGGGGGCAT | GCCCGTTCGA | GCGTCATTAC | ACCACTCCAG | CCTCGCTGGG | TATTGGGCGT | 360 |
| CTTTTCGCGG | GGGATCACTC | CCCCGCGCGC | CTCAAAGTCT | CCGGCTGAGC | GGTCTCGTCT | 420 |
| CCCAGCGTTG | TGGCATCACG | TCTCGCCGCG | GAGTTCACGA | GCCCTCACGG | CCGTTAAATC | 480 |
| ACACCTCAGG | TTGACCTCGG | ATCGGGTAGG | GATACCCGCT | GAACTTAAGC | ATATCAATAA | 540 |
| GCGGAGGA | | | | | | 548 |

( 2 ) INFORMATION FOR SEQ ID NO:2:

( i ) SEQUENCE CHARACTERISTICS:
        ( A ) LENGTH: 583 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Septoria nodorum ( i x ) FEATURE:
        ( A ) NAME/KEY: misc_feature
        ( B ) LOCATION: 1..30
        ( D ) OTHER INFORMATION: /note= "3'end of small subunit
            rRNA gene"

( i x ) FEATURE:
        ( A ) NAME/KEY: misc_feature
        ( B ) LOCATION: 31..216
        ( D ) OTHER INFORMATION: /note= "ITS 1"

( i x ) FEATURE:
        ( A ) NAME/KEY: misc_feature
        ( B ) LOCATION: 217..372
        ( D ) OTHER INFORMATION: /note= "5.8S rRNA gene"

( i x ) FEATURE:
        ( A ) NAME/KEY: misc_feature
        ( B ) LOCATION: 373..526
        ( D ) OTHER INFORMATION: /note= "ITS 2"

( i x ) FEATURE:
        ( A ) NAME/KEY: misc_feature
        ( B ) LOCATION: 527..583
        ( D ) OTHER INFORMATION: /note= "5'end of large subunit
            rRNA gene"

( x i ) SEQUENCE DESCRIPTION: SEQ ID NO:2:

| | | | | | |
|---|---|---|---|---|---|
| TCCGTAGGTG | AACCTGCGGA | AGGATCATTA | CACTCAGTAG | TTTACTACTG | TAAAAGGGGC | 60 |
| TGTTAGTCTG | TATAGCGCAA | GCTGATGAGC | AGCTGGCCTC | TTTTATCCAC | CCTTGTCTTT | 120 |
| TGCGTACCCA | CGTTTCCTCG | GCAGGCTTGC | CTGCCGGTTG | GACAAATTTA | TAACCTTTTT | 180 |
| AATTTTCAAT | CAGCGTCTGA | AAAACTTAAT | AATTACAACT | TTCAACAACG | GATCTCTTGG | 240 |
| TTCTGGCATC | GATGAAGAAC | GCAGCGAAAT | GCGATAAGTA | GTGTGAATTG | CAGAATTCAG | 300 |
| TGAATCATCG | AATCTTTGAA | CGCACATTGC | GCCCCTTGGT | ATTCCATGGG | GCATGCCTGT | 360 |
| TCGAGCGTCA | TTTGTACCCT | CAAGCTCTGC | TTGGTGTTGG | GTGTTTGTCC | TCTCCCTAGT | 420 |
| GTTTGGACTC | GCCTTAAAAT | AATTGGCAGC | CAGTGTTTTG | GTATTGAAGC | GCAGCACAAG | 480 |
| TCGCGATTCG | TAACAAACAC | TTGCGTCCAC | AAGCCTTTTT | AACTTTTGAC | CTCGGATCAG | 540 |
| GTAGGGATAC | CCGCTGAACT | TAAGCATATC | AATAAGCGGA | GGA | | 583 |

(2) INFORMATION FOR SEQ ID NO:3:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudocercosporella herpotrichoides
        (B) STRAIN: Strain W
        (C) INDIVIDUAL ISOLATE: Variant W2-1

(ix) FEATURE:
        (A) NAME/KEY: misc_feature
        (B) LOCATION: 1..30
        (D) OTHER INFORMATION: /note= "3'end of small subunit rRNA gene"

(ix) FEATURE:
        (A) NAME/KEY: misc_feature
        (B) LOCATION: 31..262
        (D) OTHER INFORMATION: /note= "ITS 1"

(ix) FEATURE:
        (A) NAME/KEY: misc_feature
        (B) LOCATION: 263..418
        (D) OTHER INFORMATION: /note= "5.8S rRNA gene"

(ix) FEATURE:
        (A) NAME/KEY: misc_feature
        (B) LOCATION: 419..569
        (D) OTHER INFORMATION: /note= "ITS 2"

(ix) FEATURE:
        (A) NAME/KEY: misc_feature
        (B) LOCATION: 570..626
        (D) OTHER INFORMATION: /note= "5'end of large subunit rRNA gene"

(xi) SEQUENCE DESCRIPTION: SEQ ID NO:3:

```
TCCGTAGGTG AACCTGCGGA AGGATCATTA ATAGAGCAAT GAACAGACAG CGCCCCGGGA      60
GAAATCCTGG GGGCTACCCT ACTTGGTAGG GTTTAGAGTC GTCAGGCCGC TCGGAGAAGC     120
CTGGTTCAGA CCTCCACCCT TGAATAAATT ACCTTTGTTG CTTTGGCAGG GCGCCTCGCG     180
CCAGCGGCTT CGGCTGTTGA GTACCTGCCA GAGGACCACA ACTCTTGTTT TTAGTGATGT     240
CTGAGTACTA TATAATAGTT AAAACTTTCA CAACGGATC  TCTTGGTTCT GGCATCGATG     300
AAGAACGCAG CGAAATGCGA TAAGTAATGT GAATTGCAGA ATTCAGTGAA TCATCGAATC     360
TTTGAACGCA CATTGCGCCC TCTGGTATTC CGGGGGGCAT GCCTGTTCGA GCGTCATTAT     420
AACCACTCAA GCTCTCGCTT GGTATTGGGG TTCGCGTCCT CGCGGCCTCT AAAATCAGTG     480
GCGGTGCCTG TCGGCTCTAC GCGTAGTAAT ACTCCTCGCG ATTGAGTCCG GTAGGTTTAC     540
TTGCCAGTAA CCCCCAATTT TTTACAGGTT GACCTCGGAT CAGGTAGGGA TACCCGCTGA     600
ACTTAAGCAT ATCAATAAGC GGAGGA                                          626
```

(2) INFORMATION FOR SEQ ID NO:4:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Pseudocercosporella herpotrichoides
  (B) STRAIN: Strain R (ix) FEATURE:
  (A) NAME/KEY: misc_feature
  (B) LOCATION: 1..30
  (D) OTHER INFORMATION: /note= "3'end of small subunit rRNA gene"

(ix) FEATURE:
  (A) NAME/KEY: misc_feature
  (B) LOCATION: 31..263
  (D) OTHER INFORMATION: /note= "ITS 1"

(ix) FEATURE:
  (A) NAME/KEY: misc_feature
  (B) LOCATION: 264..419
  (D) OTHER INFORMATION: /note= "5.8S rRNA gene"

(ix) FEATURE:
  (A) NAME/KEY: misc_feature
  (B) LOCATION: 420..570
  (D) OTHER INFORMATION: /note= "ITS 2"

(ix) FEATURE:
  (A) NAME/KEY: misc_feature
  (B) LOCATION: 571..627
  (D) OTHER INFORMATION: /note= "5'end of large subunit rRNA gene"

(xi) SEQUENCE DESCRIPTION: SEQ ID NO:4:

```
TCCGTAGGTG AACCTGCGGA AGGATCATTA ATAGAGCAAT GGATAGACAG CGCCCCGGGA    60
GAAATCCTGG GGGCCACCCT ACTTCGGTAA GGTTTAGAGT CGTCGGGCCT CTCGGAGAAG   120
CCTGGTCCAG ACCTCCACCC TTGAATAAAT TACCTTTGTT GCTTTGGCAG GGCGCCTCGC   180
GCCAGCGGCT TCGGCTGTTG AGTACCTGCC AGAGGACCAC AACTCTTGTT TTTAGTGATG   240
TCTGAGTACT ATATAATAGT TAAAACTTTC AACAACGGAT CTCTTGGTTC TGGCATCGAT   300
GAAGAACGCA GCGAAATGCG ATAAGTAATG TGAATTGCAG AATTCAGTGA ATCATCGAAT   360
CTTTGAACGC ACATTGCGCC CTCTGGTATT CCGGGGGGCA TGCCTGTTCG AGCGTCATTA   420
TAACCACTCA AGCTCTCGCT TGGTATTGGG GTTCGCGTCT CGCGGCCTC TAAAATCAGT   480
GGCGGTGCCT GTCGGCTCTA CGCGTAGTAA TACTCCTCGC GATTGAGTCC GGTAGGTTTA   540
CTTGCCAGCA ACCCCAATT TTTTACAGGT TGACCTCGGA TCAGGTAGGG ATACCCGCTG   600
AACTTAAGCA TATCAATAAG CGGAGGA                                       627
```

(2) INFORMATION FOR SEQ ID NO:5:

(i) SEQUENCE CHARACTERISTICS:
  (A) LENGTH: 534 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Mycosphaerella fijiensis (ix) FEATURE:
  (A) NAME/KEY: misc_feature (B) LOCATION: 1..30
(D) OTHER INFORMATION: /note= "3'end of small subunit rRNA gene"

(ix) FEATURE:
(A) NAME/KEY: misc_feature
(B) LOCATION: 31..171
(D) OTHER INFORMATION: /note= "ITS 1"

(ix) FEATURE:
(A) NAME/KEY: misc_feature
(B) LOCATION: 172..327
(D) OTHER INFORMATION: /note= "5.8S rRNA gene"

(ix) FEATURE:
(A) NAME/KEY: misc_feature
(B) LOCATION: 328..477
(D) OTHER INFORMATION: /note= "ITS 2"

(ix) FEATURE:
(A) NAME/KEY: misc_feature
(B) LOCATION: 478..534
(D) OTHER INFORMATION: /note= "5'end of large subunit rRNA gene"

(xi) SEQUENCE DESCRIPTION: SEQ ID NO:5:

| | | | | | | |
|---|---|---|---|---|---|---|
| TCCGTAGGTG | AACCTGCGGA | GGGATCATTA | CCGAGTGAGG | GCTCACGCCC | GACCTCCAAC | 60 |
| CCTTTGTGAA | CCACAACTTG | TTGCTTCGGG | GGCGACCTGC | CGTCGGCGGG | CGCCCCGGA | 120 |
| GGCCGTCTAA | ACACTGCATC | TTTGCGTCGG | AGTTTAAAAC | AAATCGAACA | AAACTTTCAA | 180 |
| CAACGGATCT | CTTGGTTCTG | GCATCGATGA | AGAACGCAGC | GAAATGCGAT | AAGTAATGTG | 240 |
| AATTGCAGAA | TTCAGTGAAT | CATCGAATCT | TTGAACGCAC | ATTGCGCCCT | TTGGTATTCC | 300 |
| GAAGGGCATG | CCTGTTCGAG | CGTCATTTCA | CCACTCAAGC | CTGGCTTGGT | ATTGGGCGTC | 360 |
| GCGGTTCTTC | GCGCGCCTTA | AAGTCTCCGG | CTGAGCTGTC | CGTCTCTAAG | CGTTGTGGAT | 420 |
| CTTTCAATTC | GCTTCGGAGT | GCGGGTGGCC | GCGGCCGTTA | AATCTTTATT | CAAAGGTTGA | 480 |
| CCTCGGATCA | GGTAGGGATA | CCCGCTGAAC | TTAAGCATAT | CAATAAGCGG | AGGA | 534 |

(2) INFORMATION FOR SEQ ID NO:6:

(i) SEQUENCE CHARACTERISTICS:
(A) LENGTH: 540 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) ORIGINAL SOURCE:
(A) ORGANISM: Mycosphaerella musicola (ix) FEATURE:
(A) NAME/KEY: misc_feature
(B) LOCATION: 1..30
(D) OTHER INFORMATION: /note= "3'end of small subunit rRNA gene"

(ix) FEATURE:
(A) NAME/KEY: misc_feature
(B) LOCATION: 31..180
(D) OTHER INFORMATION: /note= "ITS 1"

(ix) FEATURE:
(A) NAME/KEY: misc_feature
(B) LOCATION: 181..336
(D) OTHER INFORMATION: /note= "5.8S rRNA gene"

(ix) FEATURE:

(A) NAME/KEY: misc_feature
(B) LOCATION: 337..483
(D) OTHER INFORMATION: /note= "ITS 2"

(ix) FEATURE:
(A) NAME/KEY: misc_feature
(B) LOCATION: 484..540
(D) OTHER INFORMATION: /note= "5'end of large subunit rRNA gene"

(xi) SEQUENCE DESCRIPTION: SEQ ID NO:6:

| | | | | | |
|---|---|---|---|---|---|
| TCCGTAGGTG | AACCTGCGGG | GGGATCATTA | CCGAGTGAGG | GCTCACCCCC | GACCTCCAAC | 60
| CCTTTGTGAA | CCACACCTGT | TGCTTCGGGG | GCGACCCTGC | CGGCGAACTT | GTCGCCGGGC | 120
| GCCCCGGAG | GTCTCCTTAA | CACTGCATCT | CTGCGTCGGA | GTTCCAAACA | AATCGGACAA | 180
| AACTTTCAAC | AACGGATCTC | TTGGTTCTGG | CATCGATGAA | GAACGCAGCG | AAATGCGATA | 240
| AGTAATGTGA | ATTGCAGAAT | TCAGTGAATC | ATCGAATCTT | TGAACGCACA | TTGCGCCCTT | 300
| TGGCATTCCG | AAGGGCATGC | CTGTTCGAGC | GTCATTTCAC | CACTCAAGCC | TAGCTTGGTA | 360
| TTGGGCGCCG | CGGTGCTCCG | CGCGCCCAA | AGTCTCCGG | CTAAGCCGTC | CGTCTCTAAG | 420
| CGTTGTGGAT | TTTTCAGTTC | GCTCCGGAGC | GCGGGTGGCC | GCGGCCGTTA | AATCTTCAAA | 480
| GGTTGACCTC | GGATCAGGTA | GGGATACCCG | CTGAACTTAA | GCATATCAAT | AAGCGGAGGA | 540

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB433

(iii) HYPOTHETICAL: NO (iv) ANTI-SENSE: NO (xi) SEQUENCE DESCRIPTION: SEQ ID NO:7:

ACACTCAGTA GTTTACTACT 20

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB434

(iii) HYPOTHETICAL: NO (iv) ANTI-SENSE: NO (xi) SEQUENCE DESCRIPTION: SEQ ID NO:8:

TGTGCTGCGC TTCAATA 17

(2) INFORMATION FOR SEQ ID NO:9:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid (A) DESCRIPTION: Oligonucleotide primer JB525

(iii) HYPOTHETICAL: NO (iv) ANTI-SENSE: NO (xi) SEQUENCE DESCRIPTION: SEQ ID NO:9:

GCGACTTGTG CTGCGCTTCA ATA 23

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer JB527

(iii) HYPOTHETICAL: NO (iv) ANTI-SENSE: NO (xi) SEQUENCE DESCRIPTION: SEQ ID NO:10:

CATTACACTC AGTAGTTTAC TACT 24

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer JB445

(iii) HYPOTHETICAL: NO (iv) ANTI-SENSE: NO (xi) SEQUENCE DESCRIPTION: SEQ ID NO:11:

CTGCGTCGGA GTTTACG 17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer JB446

(iii) HYPOTHETICAL: NO (iv) ANTI-SENSE: NO (xi) SEQUENCE DESCRIPTION: SEQ ID NO:12:

CGAGGCTGGA GTGGTGT 17

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid ( A ) DESCRIPTION: Oligonucleotide primer JB526

( i i i ) HYPOTHETICAL: NO ( i v ) ANTI-SENSE: NO ( x i ) SEQUENCE DESCRIPTION: SEQ ID NO:13:

CCCAGCGAGG CTGGAGTGGT GT                                              22

( 2 ) INFORMATION FOR SEQ ID NO:14:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: Other nucleic acid
            ( A ) DESCRIPTION: Oligonucleotide primer JB536

( i i i ) HYPOTHETICAL: NO ( i v ) ANTI-SENSE: NO ( x i ) SEQUENCE DESCRIPTION: SEQ ID NO:14:

CTGGGGGCTA CCCTACTTGG TAG                                             23

( 2 ) INFORMATION FOR SEQ ID NO:15:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Other nucleic acid
            ( A ) DESCRIPTION: Oligonucleotide primer JB537

( i i i ) HYPOTHETICAL: NO ( i v ) ANTI-SENSE: NO ( x i ) SEQUENCE DESCRIPTION: SEQ ID NO:15:

GGGGGCTACC CTACTTGGTA G                                               21

( 2 ) INFORMATION FOR SEQ ID NO:16:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: Other nucleic acid
            ( A ) DESCRIPTION: Oligonucleotide primer JB538

( i i i ) HYPOTHETICAL: NO ( i v ) ANTI-SENSE: NO ( x i ) SEQUENCE DESCRIPTION: SEQ ID NO:16:

ACTTGGTAGG GTTTAGAGTC GTCA                                            24

( 2 ) INFORMATION FOR SEQ ID NO:17:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: Other nucleic acid ( A ) DESCRIPTION: Oligonucleotide primer JB539

( i i i ) HYPOTHETICAL: NO ( i v ) ANTI-SENSE: NO ( x i ) SEQUENCE DESCRIPTION: SEQ ID NO:17:

CTTCGGTAAG GTTTAGAGTC GTCG 24

( 2 ) INFORMATION FOR SEQ ID NO:18:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Oligonucleotide primer JB540

( i i i ) HYPOTHETICAL: NO ( i v ) ANTI-SENSE: NO ( x i ) SEQUENCE DESCRIPTION: SEQ ID NO:18:

GGGGGCCACC CTACTTCGGT AA 22

( 2 ) INFORMATION FOR SEQ ID NO:19:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Oligonucleotide primer JB541

( i i i ) HYPOTHETICAL: NO ( i v ) ANTI-SENSE: NO ( x i ) SEQUENCE DESCRIPTION: SEQ ID NO:19:

CCACTGATTT TAGAGGCCGC GAG 23

( 2 ) INFORMATION FOR SEQ ID NO:20:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Oligonucleotide primer JB542

( i i i ) HYPOTHETICAL: NO ( i v ) ANTI-SENSE: NO ( x i ) SEQUENCE DESCRIPTION: SEQ ID NO:20:

CCACTGATTT TAGAGGCCGC GAA 23

( 2 ) INFORMATION FOR SEQ ID NO:21:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Other nucleic acid ( A ) DESCRIPTION: Oligonucleotide primer JB543

( i i i ) HYPOTHETICAL: NO ( i v ) ANTI-SENSE: NO ( x i ) SEQUENCE DESCRIPTION: SEQ ID NO:21:

CCTGTAAAAA ATTGGGGGTT A    21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB544

( i i i ) HYPOTHETICAL: NO ( i v ) ANTI-SENSE: NO ( x i ) SEQUENCE DESCRIPTION: SEQ ID NO:22:

CCTGTAAAAA ATTGGGGGTT G    21

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB547

( i i i ) HYPOTHETICAL: NO ( i v ) ANTI-SENSE: NO ( x i ) SEQUENCE DESCRIPTION: SEQ ID NO:23:

ATTACCGAGT GAGGGCTCAC GC    22

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB548

( i i i ) HYPOTHETICAL: NO ( i v ) ANTI-SENSE: NO ( x i ) SEQUENCE DESCRIPTION: SEQ ID NO:24:

GTTGCTTCGG GGGCGACCTG    20

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid ( A ) DESCRIPTION: Oligonucleotide primer JB442

( i i i ) HYPOTHETICAL: NO ( i v ) ANTI-SENSE: NO ( x i ) SEQUENCE DESCRIPTION: SEQ ID NO:25:

TCGGGGGCGA CCTGCCG 17

( 2 ) INFORMATION FOR SEQ ID NO:26:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Oligonucleotide primer JB443

( i i i ) HYPOTHETICAL: NO ( i v ) ANTI-SENSE: NO ( x i ) SEQUENCE DESCRIPTION: SEQ ID NO:26:

CCGGAGGCCG TCTA 14

( 2 ) INFORMATION FOR SEQ ID NO:27:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Oligonucleotide primer JB545

( i i i ) HYPOTHETICAL: NO ( i v ) ANTI-SENSE: NO ( x i ) SEQUENCE DESCRIPTION: SEQ ID NO:27:

CCACAACGCT TAGAGACGGA CAG 23

( 2 ) INFORMATION FOR SEQ ID NO:28:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Oligonucleotide primer JB546

( i i i ) HYPOTHETICAL: NO ( i v ) ANTI-SENSE: NO ( x i ) SEQUENCE DESCRIPTION: SEQ ID NO:28:

CACCCGCACT CCGAAGCGAA TT 22

( 2 ) INFORMATION FOR SEQ ID NO:29:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid (A) DESCRIPTION: Oligonucleotide primer JB549

(iii) HYPOTHETICAL: NO (iv) ANTI-SENSE: NO (xi) SEQUENCE DESCRIPTION: SEQ ID NO:29:

GATCCGAGGT CAACCTTTGA ATAA 24

(2) INFORMATION FOR SEQ ID NO:30:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB444

(iii) HYPOTHETICAL: NO (iv) ANTI-SENSE: NO (xi) SEQUENCE DESCRIPTION: SEQ ID NO:30:

GGTCAACCTT TGAATAA 17

(2) INFORMATION FOR SEQ ID NO:31:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB451

(iii) HYPOTHETICAL: NO (iv) ANTI-SENSE: NO (xi) SEQUENCE DESCRIPTION: SEQ ID NO:31:

CCTTTGTGAA CCACACCT 18

(2) INFORMATION FOR SEQ ID NO:32:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB440

(iii) HYPOTHETICAL: NO (iv) ANTI-SENSE: NO (xi) SEQUENCE DESCRIPTION: SEQ ID NO:32:

CTGCCGGCGA ACTT 14

(2) INFORMATION FOR SEQ ID NO:33:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid ( A ) DESCRIPTION: Oligonucleotide primer JB449

( i i i ) HYPOTHETICAL: NO ( i v ) ANTI-SENSE: NO ( x i ) SEQUENCE DESCRIPTION: SEQ ID NO:33:

ACCCTGCCGG CGAACTT 17

( 2 ) INFORMATION FOR SEQ ID NO:34:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: Other nucleic acid
            ( A ) DESCRIPTION: Oligonucleotide primer JB448

( i i i ) HYPOTHETICAL: NO ( i v ) ANTI-SENSE: NO ( x i ) SEQUENCE DESCRIPTION: SEQ ID NO:34:

GCGACCCTGC CGGCGAAC 18

( 2 ) INFORMATION FOR SEQ ID NO:35:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: Other nucleic acid
            ( A ) DESCRIPTION: Oligonucleotide primer JB441

( i i i ) HYPOTHETICAL: NO ( i v ) ANTI-SENSE: NO ( x i ) SEQUENCE DESCRIPTION: SEQ ID NO:35:

TAGCCGGGAG ACTTTGG 17

( 2 ) INFORMATION FOR SEQ ID NO:36:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: Other nucleic acid
            ( A ) DESCRIPTION: Oligonucleotide primer JB450

( i i i ) HYPOTHETICAL: NO ( i v ) ANTI-SENSE: NO ( x i ) SEQUENCE DESCRIPTION: SEQ ID NO:36:

TCTGCGTCGG AGTTCC 16

( 2 ) INFORMATION FOR SEQ ID NO:37:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: Other nucleic acid (A) DESCRIPTION: Oligonucleotide primer JB452

(iii) HYPOTHETICAL: NO (iv) ANTI-SENSE: NO (xi) SEQUENCE DESCRIPTION: SEQ ID NO:37:

CCGCGCTCCG GAGCGAAC  18

(2) INFORMATION FOR SEQ ID NO:38:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer ITS1

(iii) HYPOTHETICAL: NO (iv) ANTI-SENSE: NO (xi) SEQUENCE DESCRIPTION: SEQ ID NO:38:

TCCGTAGGTG AACCTGCGG  19

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer ITS2

(iii) HYPOTHETICAL: NO (iv) ANTI-SENSE: NO (xi) SEQUENCE DESCRIPTION: SEQ ID NO:39:

GCTGCGTTCT TCATCGATGC  20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer ITS3

(iii) HYPOTHETICAL: NO (iv) ANTI-SENSE: NO (xi) SEQUENCE DESCRIPTION: SEQ ID NO:40:

GCATCGATGA AGAACGCAGC  20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (A) DESCRIPTION: Oligonucleotide primer ITS4

(i i i) HYPOTHETICAL: NO (i v) ANTI-SENSE: NO (x i) SEQUENCE DESCRIPTION: SEQ ID NO:41:

TCCTCCGCTT ATTGATATGC 20

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: Other nucleic acid
        (A) DESCRIPTION: Oligonucleotide primer OPB-12

(i i i) HYPOTHETICAL: NO (i v) ANTI-SENSE: NO (x i) SEQUENCE DESCRIPTION: SEQ ID NO:42:

CCTTGACGCA 10

(2) INFORMATION FOR SEQ ID NO:43:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: Other nucleic acid
        (A) DESCRIPTION: Oligonucleotide primer OPE-6

(i i i) HYPOTHETICAL: NO (i v) ANTI-SENSE: NO (x i) SEQUENCE DESCRIPTION: SEQ ID NO:43:

AAGACCCCTC 10

(2) INFORMATION FOR SEQ ID NO:44:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: Other nucleic acid
        (A) DESCRIPTION: Oligonucleotide primer OPE-12

(i i i) HYPOTHETICAL: NO (i v) ANTI-SENSE: NO (x i) SEQUENCE DESCRIPTION: SEQ ID NO:44:

TTATCGCCCC 10

(2) INFORMATION FOR SEQ ID NO:45:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: Other nucleic acid (A) DESCRIPTION: Oligonucleotide primer OPE-19

(iii) HYPOTHETICAL: NO (iv) ANTI-SENSE: NO (xi) SEQUENCE DESCRIPTION: SEQ ID NO:45:

ACCCCCGAAG 10

(2) INFORMATION FOR SEQ ID NO:46:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: Oligonucleotide primer OPE-15

(iii) HYPOTHETICAL: NO (iv) ANTI-SENSE: NO (xi) SEQUENCE DESCRIPTION: SEQ ID NO:46:

ACGCACAACC 10

(2) INFORMATION FOR SEQ ID NO:47:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudocercosporella herpotrichoides
        (B) STRAIN: Strain W
        (C) INDIVIDUAL ISOLATE: Variant W5-1

(ix) FEATURE:
        (A) NAME/KEY: misc_feature
        (B) LOCATION: 1..30
        (D) OTHER INFORMATION: /note= "3'end of small subunit
            rRNA gene"

(ix) FEATURE:
        (A) NAME/KEY: misc_feature
        (B) LOCATION: 31..263
        (D) OTHER INFORMATION: /note= "ITS 1"

(ix) FEATURE:
        (A) NAME/KEY: misc_feature
        (B) LOCATION: 264..419
        (D) OTHER INFORMATION: /note= "5.8S rRNA gene"

(ix) FEATURE:
        (A) NAME/KEY: misc_feature
        (B) LOCATION: 420..570
        (D) OTHER INFORMATION: /note= "ITS 2"

(ix) FEATURE:
        (A) NAME/KEY: misc_feature
        (B) LOCATION: 571..627
        (D) OTHER INFORMATION: /note= "5'end of large subunit
            rRNA gene"

(xi) SEQUENCE DESCRIPTION: SEQ ID NO:47:

TCCGTAGGTG AACCTGCGGA AGGATCATTA ATAGAGCAAT GAACAGACAG CGCCCTGGGA 60

```
GAAATCCTGG GGGCTACCCT ACTTCGGTAG GGTTTAGAGT CGTCAGGCCT CTCGGAGAAG    120

CCTGGTTCAG ACCTCCACCC TTGAATAAAT TACCTTTGTT GCTTTGGCAG GGCGCCTCGC    180

GCCAGCGGCT TCGGCTGTTG AGTACCTGCC AGAGGACCAC AACTCTTGTT TTTAGTGATG    240

TCTGAGTACT ATATAATAGT TAAAACTTTC AACAACGGAT CTCTTGGTTC TGGCATCGAT    300

GAAGAACGCA GCGAAATGCG ATAAGTAATG TGAATTGCAG AATTCAGTGA ATCATCGAAT    360

CTTTGAACGC ACATTGCGCC CTCTGGTATT CCGGGGGGCA TGCCTGTTCG AGCGTCATTA    420

TAACCACTCA AGCTCTCGCT TGGTATTGGG GTTCGCGTCC TCGCGGCCTC TAAAATCAGT    480

GGCGGTGCCT CTCGGCTCTA CGCGTAGTAA TACTCCTCGC GATTGAGTCC GGTAGGTTTA    540

CTTGCCAGTA ACCCCCAATT TTTTACAGGT TGACCTCGGA TCAGGTAGGG ATACCCGCTG    600

AACTTAAGCA TATCAATAAG CGGAGGA                                        627
```

( 2 ) INFORMATION FOR SEQ ID NO:48:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: M13 universal -20 oligonucleotide primer ( i i i ) HYPOTHETICAL: NO ( i v ) ANTI-SENSE: NO ( x i ) SEQUENCE DESCRIPTION: SEQ ID NO:48:

```
GTAAAACGAC GGCCAGT                                                    17
```

( 2 ) INFORMATION FOR SEQ ID NO:49:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: M13 universal reverse oligonucleotide primer ( i i i ) HYPOTHETICAL: NO ( i v ) ANTI-SENSE: NO ( x i ) SEQUENCE DESCRIPTION: SEQ ID NO:49:

```
AACAGCTATG ACCATG                                                     16
```

( 2 ) INFORMATION FOR SEQ ID NO:50:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB563"

( i i i ) HYPOTHETICAL: NO ( x i ) SEQUENCE DESCRIPTION: SEQ ID NO:50:

```
CTTGCCTGCC GGTTGGACAA ATT                                             23
```

( 2 ) INFORMATION FOR SEQ ID NO:51:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide JB564"

( i i i ) HYPOTHETICAL: NO ( x i ) SEQUENCE DESCRIPTION: SEQ ID NO:51:

CTCAGTAGTT TACTACTGTA AAAGG 25

( 2 ) INFORMATION FOR SEQ ID NO:52:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide JB565"

( i i i ) HYPOTHETICAL: NO ( x i ) SEQUENCE DESCRIPTION: SEQ ID NO:52:

CTTCTGGACG CAAGTGTTTG TTAC 24

( 2 ) INFORMATION FOR SEQ ID NO:53:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide JB566"

( i i i ) HYPOTHETICAL: NO ( x i ) SEQUENCE DESCRIPTION: SEQ ID NO:53:

GTTTTTAGTG GAACTTCTGA GT 22

( 2 ) INFORMATION FOR SEQ ID NO:54:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide JB567"

( i i i ) HYPOTHETICAL: NO ( x i ) SEQUENCE DESCRIPTION: SEQ ID NO:54:

CGCAGGAACC CTAAACTCT 19

( 2 ) INFORMATION FOR SEQ ID NO:55:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
  ( A ) DESCRIPTION: /desc = "Oligonucleotide primer JB568"

( i i i ) HYPOTHETICAL: NO ( x i ) SEQUENCE DESCRIPTION: SEQ ID NO:55:

GCCCGCCGCA GG          12

( 2 ) INFORMATION FOR SEQ ID NO:56:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB569"

( i i i ) HYPOTHETICAL: NO ( x i ) SEQUENCE DESCRIPTION: SEQ ID NO:56:

RTWWTTWRTG GAMYYTCTGA GT          22

( 2 ) INFORMATION FOR SEQ ID NO:57:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB570"

( i i i ) HYPOTHETICAL: NO ( x i ) SEQUENCE DESCRIPTION: SEQ ID NO:57:

TATGTTGCCT CGGCGG          16

( 2 ) INFORMATION FOR SEQ ID NO:58:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB571"

( i i i ) HYPOTHETICAL: NO ( x i ) SEQUENCE DESCRIPTION: SEQ ID NO:58:

TAACGATATG TAAATTACTA CGCT          24

( 2 ) INFORMATION FOR SEQ ID NO:59:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB572"

( i i i ) HYPOTHETICAL: NO ( x i ) SEQUENCE DESCRIPTION: SEQ ID NO:59:

AAGTTGGGGT TTAACGGC     18

( 2 ) INFORMATION FOR SEQ ID NO:60:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB 573"

( i i i ) HYPOTHETICAL: NO ( x i ) SEQUENCE DESCRIPTION: SEQ ID NO:60:

AGCGAGCCCG CCAC     14

( 2 ) INFORMATION FOR SEQ ID NO:61:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB574"

( i i i ) HYPOTHETICAL: NO ( x i ) SEQUENCE DESCRIPTION: SEQ ID NO:61:

CCATTGTGAA CGTTACCTAT AC     22

( 2 ) INFORMATION FOR SEQ ID NO:62:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB575"

( i i i ) HYPOTHETICAL: NO ( x i ) SEQUENCE DESCRIPTION: SEQ ID NO:62:

CGACCAGAGC GAGATGTA     18

( 2 ) INFORMATION FOR SEQ ID NO:63:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB576"

( i i i ) HYPOTHETICAL: NO ( x i ) SEQUENCE DESCRIPTION: SEQ ID NO:63:

```
GTGAACATAC  CTTATGTTGC  C                                                        2 1
```

( 2 ) INFORMATION FOR SEQ ID NO:64:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB577"

( i i i ) HYPOTHETICAL: NO ( x i ) SEQUENCE DESCRIPTION: SEQ ID NO:64:

```
GTTGCCTCGG  CGGATC                                                               1 6
```

( 2 ) INFORMATION FOR SEQ ID NO:65:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB578"

( i i i ) HYPOTHETICAL: NO ( x i ) SEQUENCE DESCRIPTION: SEQ ID NO:65:

```
CCGCGACGAT  TACCAG                                                               1 6
```

( 2 ) INFORMATION FOR SEQ ID NO:66:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB538'"

( i i i ) HYPOTHETICAL: NO ( x i ) SEQUENCE DESCRIPTION: SEQ ID NO:66:

```
TGACGACTCT  AAACCCTACC  A                                                        2 1
```

( 2 ) INFORMATION FOR SEQ ID NO:67:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB539'"

( i i i ) HYPOTHETICAL: NO ( x i ) SEQUENCE DESCRIPTION: SEQ ID NO:67:

```
CGACGACTCT  AAACCTTACC  G                                                        2 1
```

( 2 ) INFORMATION FOR SEQ ID NO:68:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer W130"

( i i i ) HYPOTHETICAL: NO ( x i ) SEQUENCE DESCRIPTION: SEQ ID NO:68:

ATTCAAGGGT GGAGGTCTGA    20

( 2 ) INFORMATION FOR SEQ ID NO:69:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer R130"

( i i i ) HYPOTHETICAL: NO ( x i ) SEQUENCE DESCRIPTION: SEQ ID NO:69:

ATTCAAGGGT GGAGGTCTGG    20

( 2 ) INFORMATION FOR SEQ ID NO:70:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB538'15"

( i i i ) HYPOTHETICAL: NO ( x i ) SEQUENCE DESCRIPTION: SEQ ID NO:70:

CTCTAAACCC TACCA    15

( 2 ) INFORMATION FOR SEQ ID NO:71:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer JB539'15"

( i i i ) HYPOTHETICAL: NO ( x i ) SEQUENCE DESCRIPTION: SEQ ID NO:71:

CTCTAAACCT TACCG    15

( 2 ) INFORMATION FOR SEQ ID NO:72:

( i ) SEQUENCE CHARACTERISTICS:
        ( A ) LENGTH: 15 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotide primer JB553"

( i i i ) HYPOTHETICAL: NO ( x i ) SEQUENCE DESCRIPTION: SEQ ID NO:72:

GTGGTCCTCT GGCAG    15

( 2 ) INFORMATION FOR SEQ ID NO:73:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotide primer JB554"

( i i i ) HYPOTHETICAL: NO ( x i ) SEQUENCE DESCRIPTION: SEQ ID NO:73:

CTCAACAGCC GAAGC    15

( 2 ) INFORMATION FOR SEQ ID NO:74:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotide primer JB555"

( i i i ) HYPOTHETICAL: NO ( x i ) SEQUENCE DESCRIPTION: SEQ ID NO:74:

GGGTGGAGGT CTGA    14

( 2 ) INFORMATION FOR SEQ ID NO:75:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotide primer JB556"

( i i i ) HYPOTHETICAL: NO ( x i ) SEQUENCE DESCRIPTION: SEQ ID NO:75:

GGTGGAGGTC TGG    13

( 2 ) INFORMATION FOR SEQ ID NO:76:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid
    ( A ) DESCRIPTION: /desc = "Oligonucleotide primer JB561"

( i i i ) HYPOTHETICAL: NO ( x i ) SEQUENCE DESCRIPTION: SEQ ID NO:76:

TGGAGGTCTG GACCA 15

( 2 ) INFORMATION FOR SEQ ID NO:77:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB562"

( i i i ) HYPOTHETICAL: NO ( x i ) SEQUENCE DESCRIPTION: SEQ ID NO:77:

TGGAGGTCTG AACCA 15

( 2 ) INFORMATION FOR SEQ ID NO:78:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB559"

( i i i ) HYPOTHETICAL: NO ( x i ) SEQUENCE DESCRIPTION: SEQ ID NO:78:

AGGGTGGAGG TCTGA 15

( 2 ) INFORMATION FOR SEQ ID NO:79:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB560"

( i i i ) HYPOTHETICAL: NO ( x i ) SEQUENCE DESCRIPTION: SEQ ID NO:79:

AGGGTGGAGG TCTGG 15

( 2 ) INFORMATION FOR SEQ ID NO:80:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Oligonucleotide primer JB557"

( i i i ) HYPOTHETICAL: NO ( x i ) SEQUENCE DESCRIPTION: SEQ ID NO:80:

TTCTCCGAGA GGCCT 15

( 2 ) INFORMATION FOR SEQ ID NO:81:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide primer
        JB558"

( i i i ) HYPOTHETICAL: NO ( x i ) SEQUENCE DESCRIPTION: SEQ ID NO:81:

TTCTCCGAGA GGCCC 15

( 2 ) INFORMATION FOR SEQ ID NO:82:

( i ) SEQUENCE CHARACTERISTICS:
        ( A ) LENGTH: 504 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Fusarium culmorum
        ( C ) INDIVIDUAL ISOLATE: R-5106, R- 5126, and R-5146
            ( c o n s e n s u s    s e q u e n c e )

( i x ) FEATURE:
        ( A ) NAME/KEY: misc_feature
        ( B ) LOCATION: 1..12
        ( D ) OTHER INFORMATION: /note= "3'end of small subunit
        rRNA gene"

( i x ) FEATURE:
        ( A ) NAME/KEY: misc_feature
        ( B ) LOCATION: 13..161
        ( D ) OTHER INFORMATION: /note= "ITS 1"

( i x ) FEATURE:
        ( A ) NAME/KEY: misc_feature
        ( B ) LOCATION: 162..318
        ( D ) OTHER INFORMATION: /note= "5.8S rRNA gene"

( i x ) FEATURE:
        ( A ) NAME/KEY: misc_feature
        ( B ) LOCATION: 319..472
        ( D ) OTHER INFORMATION: /note= "ITS 2"

( i x ) FEATURE:
        ( A ) NAME/KEY: misc_feature
        ( B ) LOCATION: 473..504
        ( D ) OTHER INFORMATION: /note= "5'end of large subunit
        rRNA gene"

( x i ) SEQUENCE DESCRIPTION: SEQ ID NO:82:

```
GAGGGATCAT  TACCGAGTTT  ACTRACTCCC  AAACCCCTGT  GAACDTACCT  TATGTTGCCT    60
CGGCGGATCA  GCCCGCGCCC  CGTAAAAAGG  GACGGCCCGC  CGCAGGAACC  CTAAACTCTG   120
TTTTTAGTGG  AACTTCTGAG  TATAAAAAAC  AAATAAATCA  AACTTTCAA   CAACGGATCT   180
CTTGGTTCTG  GCATCGATGA  AGAACGCAGC  AAAATGCGAT  AAGTAATGTG  AATTGCAGAA   240
TTCAGTGAAT  CATCGAATCT  TTGAACGCAC  ATTGCGCCCG  CCAGTATTCT  GGCGGGCATG   300
```

-continued

```
CCTGTTCGAG CGTCATTTCA ACCCTCAAGC CCAGCTTGGT GTTGGGAGCT GCAGTCCTGC        360

TGCACTCCCC AAATACATTG GCGGTCACGT CGRAGCTTCC ATAGCGTAGT AATTTACATA        420

TCGTTACTGG TAATCGTCGC GGCYACGCCG TTAAACCCCA ACTTCTGAAT GTTGACCTCG        480

GATCAGGTAG GAATACCCGC TGAA                                               504
```

( 2 ) INFORMATION FOR SEQ ID NO:83:

( i ) SEQUENCE CHARACTERISTICS:
        ( A ) LENGTH: 503 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Fusarium graminearum
        ( C ) INDIVIDUAL ISOLATE: R-8417, R- 8422, and R-8546
            ( c o n s e n s u s    s e q u e n c e )

( i x ) FEATURE:
        ( A ) NAME/KEY: misc_feature
        ( B ) LOCATION: 1..9
        ( D ) OTHER INFORMATION: /note= "3'end of small subunit
            rRNA gene"

( i x ) FEATURE:
        ( A ) NAME/KEY: misc_feature
        ( B ) LOCATION: 10..155
        ( D ) OTHER INFORMATION: /note= "ITS 1"

( i x ) FEATURE:
        ( A ) NAME/KEY: misc_feature
        ( B ) LOCATION: 156..312
        ( D ) OTHER INFORMATION: /note= "5.8S rRNA gene"

( i x ) FEATURE:
        ( A ) NAME/KEY: misc_feature
        ( B ) LOCATION: 313..466
        ( D ) OTHER INFORMATION: /note= "ITS 2"

( i x ) FEATURE:
        ( A ) NAME/KEY: misc_feature
        ( B ) LOCATION: 467..503
        ( D ) OTHER INFORMATION: /note= "5'end of large subunit
            rRNA gene"

( x i ) SEQUENCE DESCRIPTION: SEQ ID NO:83:

```
GGATCATTAC CGAGTTTACW SACTCCCAAA CCCCTGTGAA CATACCTTAT GTTGCCTCGG         60

CGGATCAGCC CGCGCCCCGA AAGGGACGGC CGCCGCAGG  AACCCTAAAC TCTGTTTTTA        120

GTGGAACTTC TGAGTATAAA AAACAAATAA ATCAAAACTT TCAACAACGG ATCTCTTGGT        180

KCTGGCATCG ATGAAGAACG CASCRAAATG CGATAAGTAA TGTGWATTGC AGAATTCAGT        240

GAATCAWCGA ATCTTTGAAC GCWSATTGCK MCCRCCAGTA TTCTGGCGGG CATGCCTGTT        300

CGAGCGTCAT TTCAACCCTC AAGCCCAGVT TGGTGTKGGG GARYTGCAGK CCTRYTKCAC        360

TCCCCAAATA ARTTGGCGGT CACGTCGAAC TTCCATAGCG TAGTAAGTTA CACATCGTTA        420

CTGGTAATCG TCGCGGCTAC GCCGTTAAAC CCCAACTTCT GAATGTTGAC CTCGGATCAG        480

GTAGGAATAC CGCTGAAGG  TAA                                                503
```

( 2 ) INFORMATION FOR SEQ ID NO:84:

( i ) SEQUENCE CHARACTERISTICS:
        ( A ) LENGTH: 545 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
 ( A ) ORGANISM: Fusarium moniliforme
 ( C ) INDIVIDUAL ISOLATE: 4551

( v i i ) IMMEDIATE SOURCE:
 ( B ) CLONE: pCRFMON1

( i x ) FEATURE:
 ( A ) NAME/KEY: misc_feature
 ( B ) LOCATION: 1..30
 ( D ) OTHER INFORMATION: /note= "3'end of small subunit rRNA gene"

( i x ) FEATURE:
 ( A ) NAME/KEY: misc_feature
 ( B ) LOCATION: 31..178
 ( D ) OTHER INFORMATION: /note= "ITS 1"

( i x ) FEATURE:
 ( A ) NAME/KEY: misc_feature
 ( B ) LOCATION: 179..335
 ( D ) OTHER INFORMATION: /note= "5.8S rRNA gene"

( i x ) FEATURE:
 ( A ) NAME/KEY: misc_feature
 ( B ) LOCATION: 336..488
 ( D ) OTHER INFORMATION: /note= "ITS 2"

( i x ) FEATURE:
 ( A ) NAME/KEY: misc_feature
 ( B ) LOCATION: 489..545
 ( D ) OTHER INFORMATION: /note= "5'end of large subunit rRNA gene"

( x i ) SEQUENCE DESCRIPTION: SEQ ID NO:84:

```
TCCGTAGGTG AACCTGCGGA GGGATCATTA CCGAGTTTAC AACTCCCAAA CCCCTGTGAA      60
CATACCTTAT GTTGCCTCGG CGGATCAGCC CGCGCCCCGT AAAAAGGGAC GGCCCGCCGC     120
AGGAACCCTA AACTCTGTTT TTAGTGGAAC TTCTGAGTAT AAAAAACAAA TAAATCAAAA     180
CTTTCAACAA CGGATCTCTT GGTTCTGGCA TCGATGAAGA ACGCAGCAAA ATGCGATAAG     240
TAATGTGAAT TGCAGAATTC AGTGAATCAT CGAATCTTTG AACGCACATT GCGCCCGCCA     300
GTATTCTGGC GGGCATGCCT GTTCGAGCGT CATTTCAACC CTCAAGCCCA GCTTGGTGTT     360
GGGAGCTGCA GTCCTGCTGC ACTCCCCAAA TACATTGGCG GTCACGTCGA GCTTCCATAG     420
CGTAGTAATT TACACATCGT TACTGGTAAT CGTCGCGGCC ACGCCGTTAA ACCCCAACTT     480
CTGAATGTTG ACCTCGGATC AGGTAGGAAT ACCCGCTGAA CTTAAGCATA TCAATAAGCG     540
GAGGA                                                                 545
```

( 2 ) INFORMATION FOR SEQ ID NO:85:

( i ) SEQUENCE CHARACTERISTICS:
 ( A ) LENGTH: 556 base pairs
 ( B ) TYPE: nucleic acid
 ( C ) STRANDEDNESS: single
 ( D ) TOPOLOGY: linear ( i i ) MOLECULE TYPE: DNA (genomic)

( v i ) ORIGINAL SOURCE:
 ( A ) ORGANISM: Microdochium nivale
 ( C ) INDIVIDUAL ISOLATE: 72, 520, and 18222 (consensus sequence)

( v i i ) IMMEDIATE SOURCE:
 ( B ) CLONE: pCRMniv72(5-2), pCRMniv520(4-2), and pCRMniv18222(6-2)

( i x ) FEATURE:
 ( A ) NAME/KEY: misc_feature

-continued (B) LOCATION: 1..30
(D) OTHER INFORMATION: /note= "3'end of small subunit rRNA gene"

(ix) FEATURE:
(A) NAME/KEY: misc_feature
(B) LOCATION: 31..175
(D) OTHER INFORMATION: /note= "ITS 1"

(ix) FEATURE:
(A) NAME/KEY: misc_feature
(B) LOCATION: 176..332
(D) OTHER INFORMATION: /note= "5.8S rRNA gene"

(ix) FEATURE:
(A) NAME/KEY: misc_feature
(B) LOCATION: 333..499
(D) OTHER INFORMATION: /note= "ITS 2"

(ix) FEATURE:
(A) NAME/KEY: misc_feature
(B) LOCATION: 500..556
(D) OTHER INFORMATION: /note= "5'end of large subunit rRNA gene"

(xi) SEQUENCE DESCRIPTION: SEQ ID NO:85:

| | | | | | | |
|---|---|---|---|---|---|---|
| TCCGTAGGTG | AACCTGCGGA | GGGATCATTA | CTGAGTTTTT | AACTCTCCAA | ACCATGTGAA | 60 |
| CTTACCACTG | TTGCCTCGGT | GGATGGTGCT | GTCTCTCGGG | ACGGTGCCAC | CGCCGGTGGA | 120 |
| CTACCTAAAC | TCTGTTAATT | TTTGTCAATC | TGAATCAAAC | TAAGAAATAA | GTTAAAACTT | 180 |
| TCAACAACGG | ATCTCTTGGT | TCTGGCATCG | ATGAAGAACG | CAGCGAAATG | CGATAAGTAA | 240 |
| TGTGAATTGC | AGAATTCAGT | GAATCATCGA | ATCTTTGAAC | GCACATTGCG | CCCATTAGTA | 300 |
| TTCTAGTGGG | CATGCCTGTT | CGAGCGTCAT | TTCAACCCTT | AAGCCTAGCT | TAGTGTTGGG | 360 |
| AGACTGCCTA | ATACGCAGCT | CCTCAAAACC | AGTGGCGGAG | TCGGTTCGTG | CTCTGAGCGT | 420 |
| AGTAATTTTT | TATCTCGCTT | CTGCAAGCCG | GACTGGCAAC | AGCCATAAAC | CGCACCCTTC | 480 |
| GGGGCACTT | TTTAATGGTT | GACCTCGGAT | CAGGTAGGAA | TACCCGCTGA | ACTTAAGCAT | 540 |
| ATCAATAAGC | GGAGGA | | | | | 556 |

(2) INFORMATION FOR SEQ ID NO:86:

(i) SEQUENCE CHARACTERISTICS:
(A) LENGTH: 563 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Septoria avenae f. sp. tricicea
(C) INDIVIDUAL ISOLATE: ATCC#26380

( i x ) FEATURE:
( A ) NAME/KEY: misc_feature
( B ) LOCATION: 1..31
( D ) OTHER INFORMATION: /note= "3'end of small subunit rRNA gene"

( i x ) FEATURE:
( A ) NAME/KEY: misc_feature
( B ) LOCATION: 32..217
( D ) OTHER INFORMATION: /note= "ITS 1"

( i x ) FEATURE:
( A ) NAME/KEY: misc_feature
( B ) LOCATION: 218..373
( D ) OTHER INFORMATION: /note= "5.8S rRNA gene"

(ix) FEATURE:
  (A) NAME/KEY: misc_feature
  (B) LOCATION: 374..529
  (D) OTHER INFORMATION: /note= "ITS 2"

(ix) FEATURE:
  (A) NAME/KEY: misc_feature
  (B) LOCATION: 530..563
  (D) OTHER INFORMATION: /note= "5'end of large subunit rRNA gene"

(xi) SEQUENCE DESCRIPTION: SEQ ID NO:86:

| | | | | | | |
|---|---|---|---|---|---|---|
| TCCCGTAGGT | GAACCTGCGG | AAGGATCATT | ACACTCAGTA | GTTTACTACT | GTAAAGGAGG | 60 |
| CTGTTAGTCT | GTATAGCGCA | AGCTGATGAG | CAGCTAGCCT | CTTTTATCCA | CCCTTGTCTT | 120 |
| TTGCGTACCC | ACGTTTCCTC | GGCAGGCTTG | CCTGCCGATT | GGACAAACCT | ATAACCTTTT | 180 |
| TAATTTTCAA | TCAGCGTCTG | AAAAACTTAA | TAATTACAAC | TTTCAACAAC | GGATCTCTTG | 240 |
| GTTCTGGCAT | CGATGAAGAA | CGCAGCGAAA | TGCGATAAGT | AGTGTGAATT | GCAGAATTCA | 300 |
| GTGAATCATC | GAATCTTTGA | ACGCACATTG | CGCCCCTTGG | TATTCCATGG | GGCATGCCTG | 360 |
| TTCGAGCGTC | ATTTGTACCC | TCAAGCTCTG | CTTGGTGTTG | GGTGTTTGTC | CTCTCCCTAG | 420 |
| TGTTTGGACT | CGCCTTAAAA | TAATTGGCAG | CCAGTGTTTT | GGTAYTGAAG | CGCAGCACAA | 480 |
| GTCGCGATTC | TTATCAAATA | CTTGCGTCCA | CAAGCCCTTT | TTTAACTTTT | GACCTCGGAT | 540 |
| CAGGTAGGAG | ACCGCTGACT | TAA | | | | 563 |

(2) INFORMATION FOR SEQ ID NO:87:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer JB605"

(xi) SEQUENCE DESCRIPTION: SEQ ID NO:87:

CCAAACCATG TGAACTTACC                                                        20

(2) INFORMATION FOR SEQ ID NO:88:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer JB606"

(xi) SEQUENCE DESCRIPTION: SEQ ID NO:88:

GGACTACCTA AACTCTGTT                                                         19

(2) INFORMATION FOR SEQ ID NO:89:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer JB607"

(xi) SEQUENCE DESCRIPTION: SEQ ID NO:89:

AGGGATCATT ACCGAGTTT                                                         19

( 2 ) INFORMATION FOR SEQ ID NO:90:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer JB609"

( x i ) SEQUENCE DESCRIPTION: SEQ ID NO:90:

TCCGGCTTGC AGAAGCGAG                                            19

( 2 ) INFORMATION FOR SEQ ID NO:91:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer JB610"

( x i ) SEQUENCE DESCRIPTION: SEQ ID NO:91:

GAAGGGTGCG GTTTATGGCT                                        20

( 2 ) INFORMATION FOR SEQ ID NO:92:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer JB611"

( x i ) SEQUENCE DESCRIPTION: SEQ ID NO:92:

GCCACCGCCG GTGGAC                                                  16

( 2 ) INFORMATION FOR SEQ ID NO:93:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer JB612"

( x i ) SEQUENCE DESCRIPTION: SEQ ID NO:93:

GGTGCTGTCT CTCGGGAC                                             18

( 2 ) INFORMATION FOR SEQ ID NO:94:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer JB613"

( x i ) SEQUENCE DESCRIPTION: SEQ ID NO:94:

AGTCAATCTG AATCAAACTA AG                                    22

( 2 ) INFORMATION FOR SEQ ID NO:95:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer JB614"

( x i ) SEQUENCE DESCRIPTION: SEQ ID NO:95:

CTAAACTCTG TTAATTTTTG TCAA        24

( 2 ) INFORMATION FOR SEQ ID NO:96:

( i ) SEQUENCE CHARACTERISTICS:
        ( A ) LENGTH: 546 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: Fusarium poae
        ( C ) INDIVIDUAL ISOLATE: T-427, T- 534, and T-756 (consensus
            sequence)

( v i i ) IMMEDIATE SOURCE:
        ( B ) CLONE: pCRFpoaeT427(1-2), pCRFpoaeT534(2-2), and
            pCRFpoaeT756(3-1)

( i x ) FEATURE:
        ( A ) NAME/KEY: misc_feature
        ( B ) LOCATION: 1..30
        ( D ) OTHER INFORMATION: /note= "3'end of small subunit
            rRNA gene"

( i x ) FEATURE:
        ( A ) NAME/KEY: misc_feature
        ( B ) LOCATION: 31..180
        ( D ) OTHER INFORMATION: /note= "ITS 1"

( i x ) FEATURE:
        ( A ) NAME/KEY: misc_feature
        ( B ) LOCATION: 181..337
        ( D ) OTHER INFORMATION: /note= "5.8S rRNA gene"

( i x ) FEATURE:
        ( A ) NAME/KEY: misc_feature
        ( B ) LOCATION: 338..489
        ( D ) OTHER INFORMATION: /note= "ITS 2"

( i x ) FEATURE:
        ( A ) NAME/KEY: misc_feature
        ( B ) LOCATION: 490..546
        ( D ) OTHER INFORMATION: /note= "5'end of large subunit
            rRNA gene"

( x i ) SEQUENCE DESCRIPTION: SEQ ID NO:96:

```
TCCGTAGGTG  AACCTGCGGA  GGGATCATTA  CCGAGTTTAC  AACTCCCAAA  CCCCTGTGAA    60
CATACCTTTA  TGTTGCCTCG  GCGGATCAGC  CCGCGCCCCG  TAAACGGGA   CGGCCCGCCG   120
CAGGAAACCC  TAAACTCTGT  TTTTAGTGGA  ACTTCTGAGT  ATAAAAAACA  AATAAATCAA   180
AACTTTCAAC  AACGGATCTC  TTGGTTCTGG  CATCGATGAA  GAACGCAGCA  AAATGCGATA   240
AGTAATGTGA  ATTGCAGAAT  TCAGTGAATC  ATCGAATCTT  TGAACGCACA  TTGCGCCCGC   300
CAGTATTCTG  GCGGGCATGC  CTGTTCGAGC  GTCATTTCAA  CCCTCAAGCC  CAGCTTGGTG   360
TTGGGATCTG  TGTGCAAACA  CAGTCCCCAA  ATTGATTGGC  GGTCACGTCG  AGCTTCCATA   420
```

| | | | | |
|---|---|---|---|---|
| GCGTAGTAAT | TTACACATCG | TTACTGGTAA | TCGTCGCGGC | CACGCCGTTA AACCCCAACT | 480 |
| TCTGAATGTT | GACCTCGGAT | CAGGTAGGAA | TACCCGCTGA | ACTTAAGCAT ATCAATAAGC | 540 |
| GGAGGA | | | | | 546 |

What is claimed is:

1. A DNA molecule isolated from the ribosomal RNA gene region of a fungal pathogen, wherein said DNA molecule is selected from the group consisting of: ITS1 of *Fusarium culmorum*, ITS2 of *Fusarium culmorum*, ITS1 of *Fusarium graminearum*, ITS2 of *Fusarium graminearum*, ITS1 of *Fusarium moniliforme*, ITS2 of *Fusarium moniliforme*, ITS1 of *Septoria avenae*, ITS2 of *Septoria avenae*, ITS1 of *Microdochium nivale*, and ITS2 of *Microdochium nivale*.

2. An Internal Transcribed Spacer sequence isolated from the ribosomal RNA gene region of a fungal pathogen, wherein said Internal Transcribed Spacer sequence is selected from the group consisting of: nucleotides 31-161 of SEQ ID NO:82, nucleotides 319-472 of SEQ ID NO:82, nucleotides 10-155 of SEQ ID NO:83, nucleotides 313-466 of SEQ ID NO:83, nucleotides 31-178 of SEQ ID NO:84, nucleotides 336-488 of SEQ ID NO:84, nucleotides 31-217 of SEQ ID NO:86, and nucleotides 374-529 of SEQ ID NO:86.

3. A method for detecting *F. graminearum*, *F. culmorum*, *F. monoliforme*, *F. poae*, *F. avenaceum*, and *M. nivale*, comprising the steps of:

(a) isolating DNA from a plant leaf infected with at least one of the following pathogens: *F. graminearum*, *F. culmorum*. *F. monoliforme*. *F. poae*, *F. avenaceum*, and *M. nivale*;

(b) amplifying a part of the Internal Transcribed Spacer sequence of the pathogen or pathogens using said DNA as a template in a polymerase chain reaction with a pair of oligonucleotide primers selected from the group of primer pairs consisting of:
SEQ ID NO:53 and SEQ ID NO:41,
SEQ ID NO:53 and SEQ ID NO:59,
SEQ ID NO:56 and SEQ ID NO:41,
SEQ ID NO:56 and SEQ ID NO:59,
SEQ ID NO:38 and SEQ ID NO:59,
SEQ ID NO:53 and SEQ ID NO:58,
SEQ ID NO:56 and SEQ ID NO:58,
SEQ ID NO:57 and SEQ ID NO:41,
SEQ ID NO:57 and SEQ ID NO:58,
SEQ ID NO:57 and SEQ ID NO:65,
SEQ ID NO:54 and SEQ ID NO:41,
SEQ ID NO:54 and SEQ ID NO:58,
SEQ ID NO:54 and SEQ ID NO:59,
SEQ ID NO:54 and SEQ ID NO:65,
SEQ ID NO:55 and SEQ ID NO:41,
SEQ ID NO:55 and SEQ ID NO:58,
SEQ ID NO:55 and SEQ ID NO:59,
SEQ ID NO:63 and SEQ ID NO:41,
SEQ ID NO:63 and SEQ ID NO:65,
SEQ ID NO:64 and SEQ ID NO:41,
SEQ ID NO:64 and SEQ ID NO:58,
SEQ ID NO:64 and SEQ ID NO:65,
SEQ ID NO:38 and SEQ ID NO:58,
SEQ ID NO:38 and SEQ ID NO:65, and
SEQ ID NO:38 and SEQ ID NO:62; and (c) detecting the pathogen or pathogens by visualizing the amplified part of the Internal Transcribed Spacer sequence.

4. A DNA molecule according to claim 1, which is either ITS1 or ITS2 of *Fusarium culmorum*.

5. A method for detecting *Fusarium culmorum*, comprising the steps of:

(a) determining the nucleotide sequence of the DNA molecule of claim 4;

(b) designing at least one PCR primer having sequence identity with at least 10 contiguous nucleotides of the nucleotide sequence determined in step (a);

(c) isolating DNA from plant tissue infected with *Fusarium culmorum*;

(d) subjecting the DNA of step (c) to polymerase chain reaction amplification using the primer or primers of step (b); and (e) detecting *Fusarium culmorum* by visualizing the product or products of the polymerase chain reaction amplification of step (d).

6. A DNA molecule according to claim 1, which is either ITS1 or ITS2 of *Fusarium graminearum*.

7. A method for detecting *Fusarium graminearum*, comprising the steps of:

(a) determining the nucleotide sequence of the DNA molecule of claim 6;

(b) designing at least one PCR primer having sequence identity with at least 10 contiguous nucleotides of the nucleotide sequence determined in step (a);

(c) isolating DNA from plant tissue infected with *Fusarium graminearum*;

(d) subjecting the DNA of step (c) to polymerase chain reaction amplification using the primer or primers of step (b); and (e) detecting *Fusarium graminearum* by visualizing the product or products of the polymerase chain reaction amplification of step (d).

8. A DNA molecule according to claim 1, which is either ITS1 or ITS2 of *Fusarium moniliforme*.

9. A method for detecting *Fusarium moniliforme*, comprising the steps of:

(a) determining the nucleotide sequence of the DNA molecule of claim 8;

(b) designing at least one PCR primer having sequence identity with at least 10 contiguous nucleotides of the nucleotide sequence determined in step (a);

(c) isolating DNA from plant tissue infected with *Fusarium moniliforme*;

(d) subjecting the DNA of step (c) to polymerase chain reaction amplification using the primer or primers of step (b); and (e) detecting *Fusarium moniliforme* by visualizing the product or products of the polymerase chain reaction amplification of step (d).

10. A DNA molecule according to claim 1, which is either ITS1 or ITS2 of *Septoria avenae*.

11. A method for detecting *Septoria avenae*, comprising the steps of:

(a) determining the nucleotide sequence of the DNA molecule of claim 10;

91

(b) designing at least one PCR primer having sequence identity with at least 10 contiguous nucleotides of the nucleotide sequence determined in step (a);

(c) isolating DNA from plant tissue infected with *Septoria avenae*;

(d) subjecting the DNA of step (c) to polymerase chain reaction amplification using the primer or primers of step (b); and (e) detecting *Septoria avenae* by visualizing the product or products of the polymerase chain reaction amplification of step (d).

12. A DNA molecule according to claim 1, which is either ITS1 or ITS2 of *Microdochium nivale*.

13. A method for detecting *Microdochium nivale*, comprising the steps of:

(a) determining the nucleotide sequence of the DNA molecule of claim 12;

(b) designing at least one PCR primer having sequence identity with at least 10 contiguous nucleotides of the nucleotide sequence determined in step (a);

(c) isolating DNA from plant tissue infected with *Microdochium nivale*;

(d) subjecting the DNA of step (c) to polymerase chain reaction amplification using the primer or primers of step (b); and (e) detecting *Microdochium nivale* by visualizing the product or products of the polymerase chain reaction amplification of step (d).

14. An Internal Transcribed Spacer sequence according to claim 2, wherein said fungal pathogen is *Fusarium culmorum* and wherein said Internal Transcribed Spacer sequence is either nucleotides 31-161 of SEQ ID NO:82 or nucleotides 319-472 of SEQ ID NO:82.

15. A method for detecting *Fusarium culmorum*, comprising the steps of:

(a) designing at least one PCR primer having sequence identity with at least 10 contiguous nucleotides of the Internal Transcribed Spacer sequence of claim 14;

(b) isolating DNA from plant tissue infected with *Fusarium culmorum*;

(c) subjecting the DNA of step (b) to polymerase chain reaction amplification using the primer or primers of step (a); and (d) detecting *Fusarium culmorum* by visualizing the product or products of the polymerase chain reaction amplification of step (c).

16. An Internal Transcribed Spacer sequence according to claim 2, wherein said fungal pathogen is *Fusarium graminearum* and wherein said Internal Transcribed Spacer sequence is either nucleotides 10-155 of SEQ ID NO:83 or nucleotides 313-466 of SEQ ID NO:83.

92

17. A method for detecting *Fusarium graminearum*, comprising the steps of:

(a) designing at least one PCR primer having sequence identity with at least 10 contiguous nucleotides of the Internal Transcribed Spacer sequence of claim 16;

(b) isolating DNA from plant tissue infected with *Fusarium graminearum*;

(c) subjecting the DNA of step (b) to polymerase chain reaction amplification using the primer or primers of step (a); and (d) detecting *Fusarium graminearum* by visualizing the product or products of the polymerase chain reaction amplification of step (c).

18. An Internal Transcribed Spacer sequence according to claim 2, wherein said fungal pathogen is *Fusarium moniliforme* and wherein said Internal Transcribed Spacer sequence is either nucleotides 31-178 of SEQ ID NO:84 or nucleotides 336-488 of SEQ ID NO:84.

19. A method for detecting *Fusarium moniliforme*, comprising the steps of:

(a) designing at least one PCR primer having sequence identity with at least 10 contiguous nucleotides of the Internal Transcribed Spacer sequence of claim 18;

(b) isolating DNA from plant tissue infected with *Fusarium moniliforme*;

(c) subjecting the DNA of step (b) to polymerase chain reaction amplification using the primer or primers of step (a); and (d) detecting *Fusarium moniliforme* by visualizing the product or products of the polymerase chain reaction amplification of step (c).

20. An Internal Transcribed Spacer sequence according to claim 2, wherein said fungal pathogen is *Septoria avenae* and wherein said Internal Transcribed Spacer sequence is either nucleotides 31-217 of SEQ ID NO:86 or nucleotides 374-529 of SEQ ID NO:86.

21. A method for detecting *Septoria avenae*, comprising the steps of:

(a) designing at least one PCR primer having sequence identity with at least 10 contiguous nucleotides of the Internal Transcribed Spacer sequence of claim 20;

(b) isolating DNA from plant tissue infected with *Septoria avenae*;

(c) subjecting the DNA of step (b) to polymerase chain reaction amplification using the primer or primers of step (a); and (d) detecting *Septoria avenae* by visualizing the product or products of the polymerase chain reaction amplification of step (c).

* * * * *